US008361971B2

(12) United States Patent
Lum et al.

(10) Patent No.: US 8,361,971 B2
(45) Date of Patent: *Jan. 29, 2013

(54) TABLET FORMULATION OF EZATIOSTAT

(75) Inventors: Robert T. Lum, Palo Alto, CA (US);
Stephan D. Parent, W. Lafayette, IN (US); Chunsheng Qiao, Redwood City, CA (US); Steven R. Schow, Redwood City, CA (US)

(73) Assignee: Telik, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/246,732

(22) Filed: Sep. 27, 2011

(65) Prior Publication Data
US 2012/0021054 A1 Jan. 26, 2012

Related U.S. Application Data

(63) Continuation of application No. 13/075,116, filed on Mar. 29, 2011.

(60) Provisional application No. 61/352,377, filed on Jun. 7, 2010.

(51) Int. Cl.
*A61K 38/05* (2006.01)
*A61K 9/20* (2006.01)

(52) U.S. Cl. .................................... 514/21.91; 424/465

(58) Field of Classification Search .................. None
See application file for complete search history.

(56) References Cited

U.S. PATENT DOCUMENTS

| 5,114,003 | A | * | 5/1992 | Jackisch et al. | 206/204 |
| 5,763,570 | A | | 6/1998 | Kauvar et al. | |
| 5,955,432 | A | * | 9/1999 | Kauvar et al. | 514/7.9 |
| 5,965,164 | A | | 10/1999 | Fuisz et al. | |
| 6,627,732 | B1 | * | 9/2003 | Sakon et al. | 530/331 |
| 7,029,695 | B2 | | 4/2006 | Redelmeier et al. | |
| 7,790,905 | B2 | * | 9/2010 | Tawa et al. | 548/375.1 |
| 2006/0148719 | A1 | * | 7/2006 | Schow | 514/18 |

FOREIGN PATENT DOCUMENTS

| EP | 1 880 722 | 1/2008 |
| WO | WO95/08563 | 3/1995 |
| WO | WO2005/065639 | 7/2005 |
| WO | WO2008/090569 | 7/2008 |
| WO | WO2009/022355 | 2/2009 |
| WO | WO2009/047799 | 4/2009 |

OTHER PUBLICATIONS

Beckmann (Eng. Life Sci. 2003, 3, 113-120).*
Author Unknown, "Telik initiates Telintra Phase 2 trial in Revlimid refractory or resistant, del 5q MDS", 2011, Abstract, retrieved from Internet: URL:http://www.new-medical.net/new/20110608/Telik-initiates-Telintra-Phase-2-trial-in-Revlimid-refractory-or-resistant-del-5q-MDS.aspx.
U.S. Appl. No. 13/041,136, filed Mar. 4, 2011, Parent et al.
U.S. Appl. No. 13/094,693, filed Apr. 26, 2011, Leclerc et al.
U.S. Appl. No. 13/108,752, filed May 16, 2011, Brown et al.
U.S. Appl. No. 13/108,754, filed May 16, 2011, Brown et al.
U.S. Appl. No. 13/108,756, filed May 16, 2011, Brown et al.
Author Unknown, "Telik initiates phase I trial of ezatiostat in patients with myelodysplastic syndrome", Thomson Reuters Integrity, 2010, Retrieved from the Internet: URL:https://integrity.thomson-pharma.com/integrity/xmlxsl/pk_ref_list.xml_show_ficha_ref? p_re_id=1444034.
Author Unknown, "Dose-Ranging Study of Telintra® Tablets + Revlimid® in Patients with Non-Deletion (5q) Low to Intermediate-1 Risk Myelodysplastic Syndrome (MDS)", Clinical Trials, 2010, Retrieved from the Internet: URL:http://clinicaltrials.gov/ct2/show/NCT01062152?term=ezatiostat&rank=2.
Author Unknown, "Phase 2 Study Comparing Two Dose Schedules of Telintra™ in Myelodysplastic Syndrome (MDS)", 2008, Retrieved from the Internet: URL: http://clinicaltrials.gov/ct2/show/NCT00700206?term=ezatiostat&rank=3.
Author Unknown, "Telik reports phase II data on ezatiostat in MDS", Thomson Reuters Integrity, 2010, Retrieved from the Internet: URL:https://integrity.thomson-pharma.com/integrity/xmlxsl/pk_ref_list.xml_show_ficha_ref?p_ref_id=1513842.
Lyttle et al. "Isozyme-specific Glutathione-S-Transferase Inhibitors: Design and Synthesis," Journal of Medicinal Chemistry, American Chemical Society, 1994, 37:189-194.
Quddus et al. "Oral Ezatiostat HCI (TLK199) and Myelodysplastic syndrome: A case report of sustained hematologic response following an abbreviated exposure", Journal of Hematology & Oncology, 2010, 3:16.
Raza et al. "Phase 1 multicenter dose-escalation study of ezatiostat hydrochloride (TLK199 tablets), a novel glutathione analog prodrug, in patients with myelodysplastic syndrome", BLOOD, 2009, 113(26):6533-6540.
Raza et al. "Multilineage Hematologic Improvement (HI) by TLK199 (TELINTRA™), A Novel Glutathione Analog, in Myelodysplastic Syndrome: Phase 2 Study Results." Poster Presentation, 2005, American Society of Hematology.
Raza et al. "Phase 1 Dose Escalation Study of TLK199 Tablets (Ezatiostat HCI, TELINTRA®), a Novel Glutathione Analog, in Myelodysplastic Syndrome." Poster Presentation, 2007, American Society of Hematology.
Raza et al. "Phase 1 Dose Escalation Study of TLK199 Tablets (Telintra), a Novel Glutathione Analog, in Myelodysplastic Syndrome," Abstract #1454 appears in Blood, vol. 100, issue 11, Nov. 16, 2007.
Raza et al. "Phase 2 Randomized Multicenter Study of Extended Dosing Schedules of Oral Ezatiostat HCI (Telintra), a Glutathione Analog Prodrug GSTP1-1 Inhibitor, In Low to Intermediate-1 Risk Myelodysplastic Syndrome (MDS)", Myelodysplastic Syndromes: Poster II, Abstract 2910, Blood 2010; 116:2910a.
Raza et al. "Phase 1-2a multicenter dose-escalation study of ezatiostat hydrochloride liposomes for injection (Telintra®, TLK199), a novel glutathione analog prodrug in patients with myelodysplastic syndrome," Journal of Hematology & Oncology, 2009, 2:20.
Yoshioka et al . "Crystalline State and Polymorphism in Solid Drugs," In: "Stability of drugs and dosage forms," Kluwer Academic, 2000, ISBN: 0-306-46404-7, Chaper 2.2.11, pp. 107-108.
International Search Report dated Apr. 19, 2012 for PCT/US2011/030376 filed Mar. 29, 2011.

(Continued)

*Primary Examiner* — James H. Alstrum-Acevedo
*Assistant Examiner* — Jessica Kassa
(74) *Attorney, Agent, or Firm* — Foley & Lardner LLP

(57) ABSTRACT

Disclosed herein are tablets comprising ezatiostat hydrochloride wherein the ezatiostat hydrochloride comprises from about 75 to about 82 percent by weight of the tablet.

22 Claims, 6 Drawing Sheets

OTHER PUBLICATIONS

Kibbe, A. Croscarmellose Sodium. Handbook for Pharmaceutical Excipients, American Pharmaceutical Association, Third Edition, 2000, pp. 160-162.

Rowe, et al. Sucrose; Magnesium Stearate. Handbook of Pharmaceutical Excipients, Pharmaceutical Press, 2006, 744, pp. 430-431.

Rowe, et al. Hypromellose. Handbook of Pharmaceutical Excipients, Pharmaceutical Press, 2003, pp. 297-300.

Rowe, et al. Mannitol. Handbook of Pharmaceutical Excipients, Pharmaceutical Press, 2009, pp. 1-3.

* cited by examiner

TABLET FORMULATION OF EZATIOSTAT

CROSS-REFERENCE TO RELATED APPLICATION

This application is a continuation of U.S. application Ser. No. 13/075,116, filed Mar. 29, 2011, which claims the benefit under 35 U.S.C. §119(e) of U.S. Provisional Patent Application No. 61/352,377, filed on Jun. 7, 2010, the contents of which are incorporated herein by reference in their entirety.

FIELD OF THE INVENTION

This invention relates to tablets comprising ezatiostat hydrochloride.

STATE OF THE ART

Ezatiostat and its salts are disclosed in U.S. Pat. No. 5,763,570. Ezatiostat has the IUPAC chemical name of ethyl (2S)-2-amino-5-[[(2R)-3-benzylsulfanyl-1-[[(1R)-2-ethoxy-2-oxo-1-phenylethyl]amino]-1-oxopropan-2-yl]amino]-5-oxopentanoate.

It has been discovered that ezatiostat salts and, in particular, the hydrochloride salt, can be formed as a crystalline ansolvate, referred to as form D, which is disclosed in U.S. application Ser. No. 13/041,136, the contents of which are incorporated herein by reference in its entirety.

Ezatiostat hydrochloride (USAN) has the molecular weight of 566.1, the trademark of Telintra®, and the CAS registry number of 286942-97-0. Ezatiostat hydrochloride has been evaluated for the treatment of myelodysplastic syndrome (MDS), in a Phase I-IIa study using a liposomal formulation (U.S. Pat. No. 7,029,695), as reported at the 2005 Annual Meeting of the American Society for Hematology (Abstract #2250) and by Raza et al. in *Journal of Hematology & Oncology*, 2:20 (published online on 13 May 2009); and in a Phase I study using a tablet formulation, as reported at the 2007 Annual Meeting of the American Society for Hematology (Abstract #1454) and by Raza et al. in *Blood*, 113:6533-6540 (prepublished online on 27 Apr. 2009), and in a single patient case report by Quddus et al. in *Journal of Hematology & Oncology*, 3:16 (published online on 23 Apr. 2010). The entire disclosures of each of the patents and publications referred to in this application are incorporated into this application by reference.

The clinical tablet formulation of ezatiostat hydrochloride for treatment of MDS employs tablets containing 500 mg of ezatiostat hydrochloride. When so employed, tablet size and its ability to be swallowed by patients who are typically elderly becomes a problem. Typically, tablets employ a variety of pharmaceutically acceptable excipients which can range up to 90+ weight percent of the total weight of the tablet. When the excipients' content is so high, there is less concern about sizing the tablet as adjusting the amount of excipients can reduce the weight of the tablet and, accordingly, its size.

In the case of ezatiostat hydrochloride with its large molecular weight and the required amount of actives, tablets sized at a level suitable for oral delivery to human patients, especially elderly patients, must comprise from about 75 to 82 weight percent of that drug. This, in turn, imparts significant difficulty in preparing suitable tablets. For example, tablets containing this much of the active drug, in addition to being suitably sized, must meet pharmaceutical characteristics which include among others, flow characteristic, granulate density, granulate compressibility, suitable integrity during manufacture, shipping and storage, proper shelf-life, and suitable disintegration properties when ingested. Given the weight percent of ezatiostat hydrochloride in these tablets, the amount of excipients used to make a pharmaceutically useful tablet is strictly limited.

Accordingly, while there is a need for tablets of ezatiostat hydrochloride which permit a suitably sized tablet containing from about 75 to about 82 weight percent of drug, the ability of forming a tablet with that much active drug is exceptionally problematic.

SUMMARY OF THE INVENTION

This invention is directed to the surprising and unexpected discovery that pharmaceutically acceptable tablets of ezatiostat hydrochloride can be prepared using 75 to 82 weight percent of the drug while still maintaining all of the properties required of a tablet.

Accordingly, in one embodiment, this invention is directed to pharmaceutically acceptable tablets comprising ezatiostat hydrochloride, an intragranular excipient, and an extragranular excipient, wherein the ezatiostat hydrochloride comprises from about 75 to about 82 percent by weight of the tablet.

In another embodiment of this invention, the tablets contain from about 100 mg to about 1250 mg ezatiostat hydrochloride and employ one or more intragranular excipients and one or more extragranular excipients.

In another embodiment of this invention, the intragranular excipient comprises one or more of mannitol, croscarmellose sodium, hypromellose. In another embodiment, the intragranular excipient comprises a mixture of each of these components. The total amount of the intragranular excipient is from about 17 to about 21 weight/weight percent based on the total weight of the tablet and preferably from about 19 to about 20 weight/weight percent.

In a preferred embodiment, the amount of mannitol employed in the intragranular excipient mixture ranges from about 13 to about 15 weight/weight percent and preferably from about 13.5 to about 14.5 weight/weight percent based on the total weight of the tablet. The mannitol acts as a diluent in the intragranular agglomerate.

In a preferred embodiment, the amount of croscarmellose sodium employed in the intragranular excipient mixture ranges from about 1.5 to about 3.5 weight percent and preferably from about 2 to about 3 weight percent based on the total weight of the tablet. The croscarmellose sodium acts as a disintegrant in the intragranular agglomerate.

In a preferred embodiment, the amount of hypromellose employed in the intragranular excipient mixture ranges from about 2 to 4 weight percent and preferably from about 2.5 to about 3.5 weight percent based on the total weight of the tablet. The hypromellose acts as a binder in the intragranular agglomerate.

As per the examples below, the intragranular excipient mixture is blended with the drug to provide a cohesive agglomerate. This agglomerate is formed into granules which are then combined with an extragranular excipient mixture, blended and formed into tablets. In one embodiment, the extragranular excipients include magnesium stearate and croscarmellose sodium.

In a preferred embodiment, the amount of croscarmellose sodium employed in the extragranular excipient mixture ranges from about 1 to 4 weight percent and preferably about 1.5 to about 3.5 weight/weight percent and even more preferably about 2 to about 3 weight/weight percent based on the total weight of the tablet. The croscarmellose sodium acts as a disintegrant in the formed tablet.

In a preferred embodiment, the amount of magnesium stearate employed in the extragranular excipient mixture ranges from about 0.5 to about 1.5 weight/weight percent and preferably about 1 weight/weight percent based on the total weight of the tablet. The magnesium stearate acts as a lubricant in the formed tablet.

As used above, the total weight of the tablet is based on the amount of drug, the amount of intragranular excipients and the amount of extragranular excipients. The amount of water in the tablet is negligible. Optionally, a coating can be applied to the tablets. Any such coating is not included in the weight of the tablet for the purposes of determining the weight percentages recited herein. The optional coating includes pharmaceutically acceptable coating excipients. Preferably, such excipients include a combination of polyethylene glycol and hypromellose as coating agents.

As provided in the examples below, it has been surprisingly found that the tablets of this invention are pharmaceutically acceptable notwithstanding the very high percentage of drug employed in these tablets.

DETAILED DESCRIPTION

Figure 1:
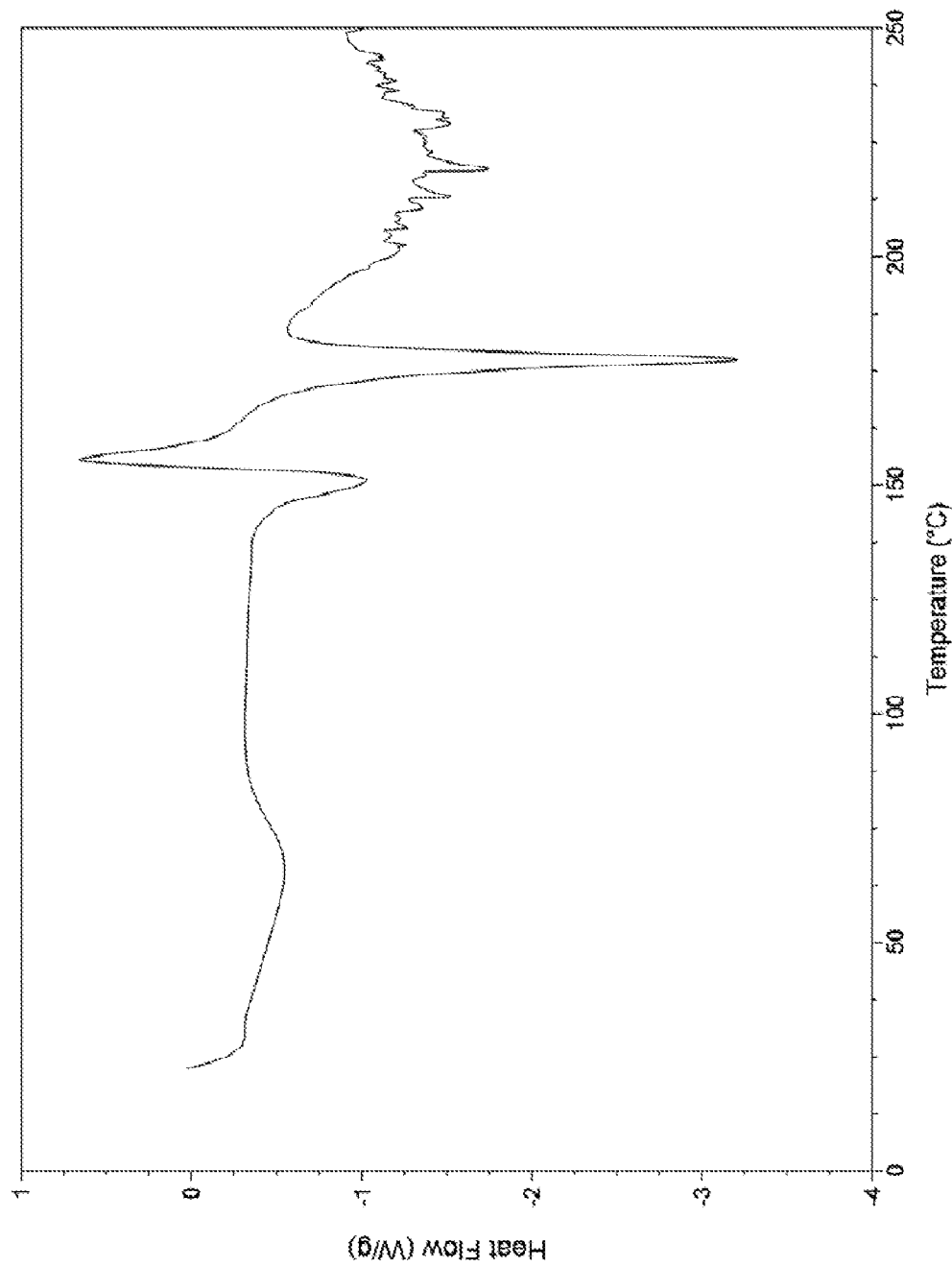
FIG. 1 is a DSC pattern of ezatiostat hydrochloride monohydrate form A.

This invention is directed to tablets comprising ezatiostat hydrochloride. However, prior to describing this invention in more detail, the following terms will first be defined.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 15%, 10%, 5% or 1%.

The singular forms "a," "an," and "the" and the like include plural referents unless the context clearly dictates otherwise. Thus, for example, reference to "a compound" includes both a single compound and a plurality of different compounds.

The "crystalline ansolvate" of ezatiostat hydrochloride is a crystalline solid form of ezatiostat hydrochloride, such as, e.g., the crystalline form D. The form D crystal lattice is substantially free of solvents of crystallization. However, any solvent present is not included in the crystal lattice and is randomly distributed outside the crystal lattice. Therefore, form D crystals in bulk may contain, outside the crystal lattice, small amounts of one or more solvents, such as the solvents used in its synthesis or crystallization. As used above, "substantially free of" and "small amounts," refers to the presence of solvents preferably less than 10,000 parts per million (ppm), or more preferably, less than 500 ppm.

"Characterization" refers to obtaining data which may be used to identify a solid form of a compound, for example, to identify whether the solid form is amorphous or crystalline and whether it is unsolvated or solvated. The process by which solid forms are characterized involves analyzing data collected on the polymorphic forms so as to allow one of ordinary skill in the art to distinguish one solid form from other solid forms containing the same material. Chemical identity of solid forms can often be determined with solution-state techniques such as $^{13}C$ NMR or $^1H$ NMR. While these may help identify a material, and a solvent molecule for a solvate, such solution-state techniques themselves may not provide information about the solid state. There are, however, solid-state analytical techniques that can be used to provide information about solid-state structure and differentiate among polymorphic solid forms, such as single crystal X-ray diffraction, X-ray powder diffraction (XRPD), solid state nuclear magnetic resonance (SS-NMR), and infrared and Raman spectroscopy, and thermal techniques such as differential scanning calorimetry (DSC), thermogravimetry (TG), melting point, and hot stage microscopy.

To "characterize" a solid form of a compound, one may, for example, collect XRPD data on solid forms of the compound and compare the XRPD peaks of the forms. For example, when only two solid forms, I and II, are compared and the form I pattern shows a peak at an angle where no peaks appear in the form II pattern, then that peak, for that compound, distinguishes form I from form II and further acts to characterize form I. The collection of peaks which distinguish form I from the other known forms is a collection of peaks which may be used to characterize form I. Those of ordinary skill in the art will recognize that there are often multiple ways, including multiple ways using the same analytical technique, to characterize solid forms. Additional peaks could also be used, but are not necessary, to characterize the form up to and including an entire diffraction pattern. Although all the peaks within an entire XRPD pattern may be used to characterize such a form, a subset of that data may, and typically is, used to characterize the form.

An XRPD pattern is an x-y graph with diffraction angle (typically °2θ) on the x-axis and intensity on the y-axis. The peaks within this pattern may be used to characterize a crystalline solid form. As with any data measurement, there is variability in XRPD data. The data are often represented solely by the diffraction angle of the peaks rather than including the intensity of the peaks because peak intensity can be particularly sensitive to sample preparation (for example, particle size, moisture content, solvent content, and preferred orientation effects influence the sensitivity), so samples of the same material prepared under different conditions may yield slightly different patterns; this variability is usually greater than the variability in diffraction angles. Diffraction angle variability may also be sensitive to sample preparation. Other sources of variability come from instrument parameters and processing of the raw X-ray data: different X-ray instruments operate using different parameters and these may lead to slightly different XRPD patterns from the same solid form, and similarly different software packages process X-ray data differently and this also leads to variability. These and other sources of variability are known to those of ordinary skill in the pharmaceutical arts. Due to such sources of variability, it is usual to assign a variability of ±0.2° 2θ to diffraction angles in XRPD patterns.

X-ray powder diffraction (XRPD) analyses were performed on a Shimadzu XRD-6000 X-ray powder diffractometer using Cu Kα radiation from a long fine focus X-ray tube, operated at 40 kV, 40 mA. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.5°-40° 2θ was used. A silicon standard was analyzed to check alignment of the instrument. Data were collected and analyzed using XRD-6000 v.4.1 software.

High-resolution XRPD analyses were also performed on a PANalytical X'Pert PRO PW3040 diffractometer, using Cu Kα radiation produced by an Optix long fine-focus tube (45 kV, 40 mA). An elliptically graded multilayer mirror was used to focus the X-rays through the specimen, which was sandwiched between 3 μm films, analyzed in transmission geometry, and rotated to optimize orientation statistics. A beam-stop and helium purge were used to minimize the air-scattering background; Soller slits (divergence slit, 0.5°; scattering slit 0.25°) were used for the incident and diffracted beams to minimize axial divergence. Diffraction patterns were collected using a scanning position-sensitive X'Celerator detector located 240 mm from the specimen, over a scan range of 1.01°-39° 2θ with a scan speed of 1.2°/min (step size 0.017° 2θ). A silicon standard was analyzed to check alignment of the instrument. Data were collected and analyzed using X'Pert PRO Data Collector v. 2.2b software. Indexing and Pawley refinement of the ezatiostat hydrochloride monohydrate XRPD pattern was performed using Match v.2.4.0 software (SSCI) and verified using ChekCell v. Nov. 1, 2004. Indexing and Pawley refinement of the crystalline ezatiostat hydrochloride ansolvate XRPD pattern was performed using DASH v. 3.1 software (Cambridge Crystallographic Data Center).

Variable-temperature XRPD (VT-XRPD) analysis was performed on a Shimadzu XRD-6000 diffractometer equipped with an Anton Paar HTK 1200 high temperature stage. The sample was packed in a ceramic holder and analyzed from 2.5°-40° 2θ at 3°/min (0.4 sec/0.02° step). The temperature was held constant during each XRPD scan. Temperature calibration was performed using vanillin and sulfapyridine standards. A silicon standard was analyzed to check alignment of the instrument; data were collected and analyzed using XRD-6000 v.4.1 software.

Differential scanning calorimetry (DSC) analyses were performed on a TA Instruments Q100 or 2920 differential scanning calorimeter, which was calibrated using indium as the reference material. The sample was placed into a standard aluminum DSC pan with an uncrimped lid, and the weight accurately recorded. The sample cell was equilibrated at 25° C. and heated under a nitrogen purge at a rate of 10° C./minute to a final temperature of 250° C. The variability of DSC data is affected by sample preparation and particularly by heating rate.

Solid-state NMR(SS-NMR) $^{13}$C cross-polarization magic angle spinning (CP/MAS) analyses were performed at room temperature on a Varian $^{UNITY}$INOVA-400 spectrometer (Larmor frequencies: $^{13}$C=100.542 MHz, $^{1}$H=399.800 MHz). The sample was packed into a 4 mm PENCIL type zirconia rotor and rotated at 12 kHz at the magic angle. The spectrum was acquired with phase modulated SPINAL-64 high power $^{1}$H decoupling during the acquisition time using a $^{1}$H pulse width of 2.2 μs (90°), a ramped amplitude cross polarization contact time of 2 ms, a 30 ms acquisition time, a 5 second delay between scans, a spectral width of 45 KHz with 2700 data points, and 200 co-added scans. The free induction decay (FID) was processed using Varian VNMR 6.1C software with 32768 points and an exponential line broadening factor of 10 Hz to improve the signal-to-noise ratio. The first three data points of the FID were back predicted using the VNMR linear prediction algorithm to produce a flat baseline. The chemical shifts of the spectral peaks were externally referenced to the carbonyl carbon resonance of glycine at 176.5 ppm. The variability of SS-NMR peaks in this experiment is considered to be ±0.2 ppm.

Karl Fischer analyses for water determination were performed on a Mettler Toledo DL39 Karl Fischer titrator. About 10-15 mg of sample was placed in the KF titration vessel containing approximately 100 mL of Hydranal®—Coulomat AD reagent and mixed for 60 seconds to ensure dissolution. The dissolved sample was then titrated by means of a generator electrode which produces iodine by electrochemical oxidation.

Thermogravimetric (TG-IR) analyses were performed on a TA Instruments model 2050 thermogravimetric (TG) analyzer interfaced to a Thermo Nicolet Magna® 560 Fourier transform infrared (FT-IR) spectrophotometer equipped with a Ever-Glo mid/far IR source, a potassium bromide beam-splitter, and a deuterated triglycine sulfate detector. The instrument was operated under a flow of helium at 90 mL/min (purge) and 10 mL/min (balance). The sample was placed in a platinum sample pan, inserted into the TG furnace, accurately weighed by the instrument, and heated from ambient at a rate of 20° C./min. The TG instrument was started first, immediately followed by the FT-IR instrument. IR spectra were collected every 12.86 seconds; and each IR spectrum represents 32 co-added scans collected at a spectral resolution of 4 cm$^{-1}$. A background scan was collected before the beginning of the experiment. Wavelength calibration was performed using polystyrene. The TG calibration standards were nickel and Alumel™.

Hot stage microscopy analysis was performed on a Linkam FTIR 600 hot stage mounted on a Leica DM LP microscope. Samples were observed using a 20× objective with cross polarizers and lambda compensator. A coverslip was then placed over the sample. Each sample was visually observed as the stage was heated. Images were captured using a SPOT Insight™ color digital camera with SPOT Software v. 3.5.8. The hot stage was calibrated using USP melting point standards.

The term "does not undergo polymorphic transformation" refers to no observable polymorphic transformation of a crystalline form, when exposed to up to about 75% relative humidity at up to about 40° C. for up to about 6 months, when analyzed by XRPD or HPLC or another equivalently sensitive technique.

"Desiccant" refers to a substance that induces or sustains a state of dryness in its local vicinity in a moderately well-sealed container. Desiccants can absorb or adsorb water, or act by a combination of the two. Desiccants may also work by other principles, such as chemical bonding of water molecules. A pre-packaged desiccant may be used to remove excessive humidity that would degrade products. Non-limiting examples of desiccants include silica gel, calcium sulfate, calcium chloride, montmorillonite clay, and molecular sieves.

"Room temperature" refers to (22±5)° C.

"Storing" or "storage" refers to storing crystalline ezatiostat hydrochloride. In a preferred embodiment, crystalline ezatiostat hydrochloride comprises ansolvate form D or a composition including the form D such that no more than about 10%, more preferably no more than about 5%, still more preferably no more than about 3%, or most preferably no more than about 1% of the ansolvate form D undergoes transformation to another compound.

Methods of the Invention

Tablet Preparation

Ezatiostat hydrochloride tablets prepared below are preferably modified capsule shaped, coated tablets containing 500 mg of ezatiostat hydrochloride.

The ezatiostat hydrochloride used in the tablets may be in hydrated or in crystalline anhydrous form (though the weights and weight percentages in the specification and claims are based on anhydrous ezatiostat hydrochloride).

A crystalline anhydrous form of ezatiostat hydrochloride may be obtained by heating hydrated ezatiostat hydrochloride to temperatures over about 125° C. (the temperature required being dependent on the initial level of hydration: about 130° C. for a polyhydrate containing approximately 5 molecules of water per molecule of ezatiostat hydrochloride to about 153° C. for ezatiostat hydrochloride monohydrate), or may be obtained by slurrying hydrated ezatiostat hydrochloride in methyl tert-butyl ether at ambient temperature or in hexanes at elevated temperatures such as 60° C. If the ezatiostat hydrochloride is crystallized at the end of its synthesis, crystalline anhydrous ezatiostat hydrochloride may be obtained by dissolution of crude hydrated ezatiostat hydrochloride in about 5.6 times its weight of ethanol, heating to about 65°-70° C., filtering, seeding with a small quantity (e.g. about 2% by weight of the initial ezatiostat hydrochloride) of crystalline anhydrous ezatiostat hydrochloride, cooling to about 40° C., adding ethyl acetate in about 13.5 times the weight of the ezatiostat hydrochloride, gradually cooling to about 20°-25° C. and then to −5°-0° C., then filtering, washing with ethyl acetate, and drying. This crystalline anhydrous form has a melting point of about 166° C., and is characterized by an orthorhombic space group ($P2_12_12$ or $P2_12_12_1$) with approximate unit cell dimensions of a=64.2±0.2 Å, b=18.3±0.1 Å, c=5.1±0.1 Å

Each tablet contains ezatiostat hydrochloride in a formulation containing mannitol, croscarmellose sodium, hypromellose, magnesium stearate, and optionally coated with mixture of hypromellose and polyethylene glycol 400 (also referred to as Opadry® Clear). Purified water, used during granulation and coating, is removed during processing. The quantitative composition of ezatiostat hydrochloride tablets is provided in Table 1.

TABLE 1

Quantitative Composition of Ezatiostat Hydrochloride Tablets

| Ingredient and Grade | Final Composition Percent (w/w) | Amount per Tablet (mg) 500 mg Tablet |
|---|---|---|
| Drug Substance | | |
| Ezatiostat hydrochloride | 76.9 | 500 |
| Intragranular Excipients | | |
| Mannitol, USP | 14.1 | 91.5 |
| Croscarmellose Sodium, NF | 2.5 | 16.23 |
| Hypromellose, USP | 3.0 | 19.5 |
| Purified Water, USP | Negligible[a] | Negligible[a] |

TABLE 1-continued

Quantitative Composition of Ezatiostat Hydrochloride Tablets

| Ingredient and Grade | Final Composition Percent (w/w) | Amount per Tablet (mg) 500 mg Tablet |
|---|---|---|
| Extragranular Excipients | | |
| Croscarmellose Sodium, NF | 2.5 | 16.3 |
| Magnesium Stearate, NF | 1.0 | 6.5 |
| Core Tablet Total | 100 | 650 |
| Optional Coating Excipients | | |
| Hypromellose, USP | 3[b] | 19.5 |
| Polyethylene Glycol 400, NF | | |
| Purified Water, USP | Negligible[a] | Negligible[a] |
| Coated Tablet Total | NA | 670 |

[a]Water is removed during processing.
[b]3% w/w of combined coating excipients.
NA = not applicable.

The inactive ingredients in ezatiostat hydrochloride tablets and the grade of those ingredients are listed in Table 2. The rationale for each of the ingredients is also provided. For the intragranular excipients, mannitol functions as a diluent, croscarmellose sodium as a disintegrant, hypromellose as a binder and purified water as the granulation fluid. Extragranular excipients include croscarmellose sodium as a disintegrant and magnesium stearate as a lubricant. Coating agents consist of hypromellose and polyethylene glycol 400. These two combined excipients are used as a product called Opadry® Clear.

The inactive ingredients conform to current compendial monograph requirements according to the USP and National Formulary (NF) and are provided in Table 2 below.

TABLE 2

Inactive Ingredients in Ezatiostat HCl Tablets

| Inactive Ingredients | Grade | Function |
|---|---|---|
| Intragranular Excipients | | |
| Mannitol | USP | Diluent |
| Croscarmellose Sodium | NF | Disintegrant |
| Hypromellose[a] | USP | Binder |
| Purified Water[b] | USP | Granulation Fluid |
| Extragranular Excipients | | |
| Croscarmellose Sodium | NF | Disintegrant |
| Magnesium Stearate | NF | Lubricant |
| Coating Excipients | | |
| Hypromellose[a,c] | USP | Coating Agent |
| Polyethylene Glycol 400[c] | NF | Coating Agent |
| Purified Water[b] | USP | Solvent |

[a]Hypromellose is also known as hydroxypropyl methylcellulose (HPMC).
[b]Water is removed during processing.
[c]Hypromellose and Polyethylene Glycol 400 are the ingredients in Opadry® Clear.

Ezatiostat hydrochloride tablets are manufactured by dry blending ezatiostat hydrochloride and the intragranular excipients, adding water and wet screening the granulate. The granulate is then dried in a fluid bed dryer and the dried granules are milled. The dried, milled granules are blended with the extragranular excipients in a V blender. After the blend is compressed into tablets, they are film coated with Opadry® Clear solution. The general manufacturing process for the tablets is discussed in Example 2.

Ezatiostat hydrochloride tablets are packed in white high density polypropylene (HDPE) bottles, with a white HDPE outer cap and polypropylene (PP) inner cap over an induction seal. Each bottle contains either 50 tablets or 150 tables for 500 mg strength. A small canister containing silica gel desiccant has been placed in the tablet bottles to reduce moisture and improve stability (shelf-life).

Ezatiostat hydrochloride tablets can be stored at 2° C.-30° C. The tablets of this invention have a shelf-life of at least 48 months when stored with a desiccant at 25° C. and 60% relative humidity. When so prepared, the tablets of this invention are suitable for pharmaceutical use including among others a suitable size and possess acceptable hardness, dissolution and shelf-life.

In one embodiment, this invention provides a pharmaceutically acceptable tablet comprising ezatiostat hydrochloride, an intragranular excipient and extragranular excipient wherein the ezatiostat hydrochloride comprises from about 75 to about 82 percent by weight of the tablet, said tablet further comprises a film coating.

In another embodiment, this invention provides a pharmaceutically acceptable tablet comprising ezatiostat hydrochloride, an intragranular excipient and extragranular excipient wherein the ezatiostat hydrochloride comprises from about 75 to about 82 percent by weight of the tablet, wherein said tablet comprises about 500 mg of ezatiostat hydrochloride. In another embodiment, the tablet comprises preferably about 750 mg, more preferably about 1 gm, and even more preferably about 1.25 gm of ezatiostat hydrochloride.

In another embodiment, this invention provides a pharmaceutically acceptable tablet comprising ezatiostat hydrochloride, an intragranular excipient and extragranular excipient wherein the ezatiostat hydrochloride comprises from about 75 to about 82 percent by weight of the tablet, wherein said tablet is stored in a container with a desiccant.

Crystalline Ansolvate

When used for treating humans, it is important that a crystalline therapeutic agent like ezatiostat hydrochloride retains its polymorphic and chemical stability, solubility, and other physicochemical properties over time and among various manufactured batches of the agent. If the physicochemical properties vary with time and among batches, the administration of a therapeutically effective dose becomes problematic and may lead to toxic side effects or to ineffective therapy, particularly if a given polymorph decomposes prior to use, to a less active, inactive, or toxic compound. Therefore, it is important to choose a form of the crystalline agent that is stable, is manufactured reproducibly, and has physicochemical properties favorable for its use as a therapeutic agent.

It has been discovered that ezatiostat salts and, in particular, the hydrochloride salt, can be formed as a crystalline ansolvate, referred to here as form D. Surprisingly, this ansolvate demonstrates superior stability and other physicochemical properties compared to the solvate crystalline forms A, B, C, E, and F. Accordingly, in one aspect, this invention provides for tablets comprising crystalline ezatiostat ansolvate salt and, in particular, the hydrochloride salt (crystalline form D). In one embodiment, the crystalline ezatiostat hydrochloride ansolvate does not undergo polymorphic transformation. In another embodiment, the crystalline ezatiostat hydrochloride ansolvate is characterized by an endothermic peak at (177±2)° C. as measured by differential scanning calorimetry. In another embodiment, the crystalline ezatiostat hydrochloride ansolvate is characterized by the substantial absence of thermal events at temperatures below the endothermic peak at (177±2)° C. as measured by differential scanning calorimetry. In another embodiment, the crystalline ezatiostat hydrochloride ansolvate is characterized by an X-ray powder diffraction peak (Cu Kα radiation) at (2.7±0.2)° 2θ. In another embodiment, the crystalline ezatiostat hydrochloride ansolvate is characterized by an X-ray powder diffraction peak (Cu Kα radiation) at (6.3±0.2)° 2θ. In another embodiment, the crystalline ezatiostat hydrochloride ansolvate is characterized by an X-ray powder diffraction pattern (Cu Kα radiation) substantially similar to that of FIG. 3 or FIG. 4. In another embodiment, the crystalline ezatiostat hydrochloride ansolvate is characterized by a solid-state $^{13}C$ nuclear magnetic resonance spectrum substantially similar to that of FIG. 5. In another embodiment, the crystalline ezatiostat hydrochloride ansolvate is characterized by at least two X-ray powder diffraction peaks (Cu Kα radiation) selected from 2.7°, 6.3°, 7.3°, 8.2°, 8.4°, 9.6°, 11.0°, and 12.7° 2θ (each ±0.2° 2θ). In another embodiment, the crystalline ezatiostat hydrochloride ansolvate is characterized by at least three X-ray powder diffraction peaks (Cu Kα radiation) selected from 2.7°, 6.3°, 7.3°, 8.2°, 8.4°, 9.6°, 11.0°, and 12.7° 2θ (each ±0.2° 2θ). In another embodiment, the crystalline ezatiostat hydrochloride ansolvate is characterized by at least one X-ray powder diffraction peak (Cu Kα radiation) selected from 2.7°, 6.3°, 7.3°, 8.2°, 8.4°, 9.6°, 11.0°, and 12.7° 2θ (each ±0.2° 2θ). In another embodiment, the crystalline ezatiostat hydrochloride is characterized by at least two X-ray powder diffraction peaks (Cu Kα radiation) selected from 2.7°, 6.3°, 7.3°, 8.2°, 8.4°, 9.6°, 11.0°, and 12.7° 2θ (each ±0.2° 2θ). In another embodiment, the crystalline ezatiostat hydrochloride ansolvate is characterized by at least three X-ray powder diffraction peaks (Cu Kα radiation) selected from 2.7°, 6.3°, 7.3°, 8.2°, 8.4°, 9.6°, 11.0°, and 12.7° 2θ (each ±0.2° 2θ).

In one embodiment, this invention provides a pharmaceutically acceptable tablet comprising ezatiostat hydrochloride, an intragranular excipient, and extragranular excipient, wherein the ezatiostat hydrochloride comprises from about 75 to about 82 percent by weight of the tablet and the ezatiostat hydrochloride comprises crystalline form D. In a further embodiment, said tablet contains from about 100 mg to about 1250 mg of ezatiostat hydrochloride.

In another embodiment, this invention provides a pharmaceutically acceptable tablet comprising ezatiostat hydrochloride, an intragranular excipient, and extragranular excipient, wherein the ezatiostat hydrochloride comprises from about 75 to about 82 percent by weight of the tablet and the ezatiostat hydrochloride comprises crystalline form D, wherein intragranular excipient is selected from one or more of mannitol, croscarmellose sodium, and hypromellose. In a further embodiment, the intragranular excipient comprises a mixture of mannitol, croscarmellose sodium, and hypromellose. In another embodiment, the intragranular excipient comprises from about 17 to about 21 percent by weight of the tablet. In another embodiment, the intragranular excipient comprises from about 19 to about 20 percent by weight of the tablet.

In another embodiment, this invention provides a pharmaceutically acceptable tablet comprising ezatiostat hydrochloride, an intragranular excipient, and extragranular excipient, wherein the ezatiostat hydrochloride comprises from about 75 to about 82 percent by weight of the tablet and the ezatiostat hydrochloride comprises crystalline form D, wherein the intragranular excipient comprises mannitol and the amount of mannitol ranges from about 13 to about 15 percent by weight of the tablet.

In another embodiment, this invention provides a pharmaceutically acceptable tablet comprising ezatiostat hydrochloride, an intragranular excipient, and extragranular excipient, wherein the ezatiostat hydrochloride comprises from about 75 to about 82 percent by weight of the tablet and the ezatiostat hydrochloride comprises crystalline form D, wherein the intragranular excipient comprises croscarmellose sodium and the amount of croscarmellose sodium ranges from about 1.5 to about 3.5 percent by weight of the tablet.

In another embodiment, this invention provides a pharmaceutically acceptable tablet comprising ezatiostat hydrochloride, an intragranular excipient, and extragranular excipient, wherein the ezatiostat hydrochloride comprises from about 75 to about 82 percent by weight of the tablet and the ezatiostat hydrochloride comprises crystalline form D, wherein the intragranular excipient comprises hypromellose and the amount of hypromellose ranges from about 2 to about 4 percent by weight of the tablet.

In another embodiment, this invention provides a pharmaceutically acceptable tablet comprising ezatiostat hydrochloride, an intragranular excipient, and extragranular excipient, wherein the ezatiostat hydrochloride comprises from about 75 to about 82 percent by weight of the tablet and the ezatiostat hydrochloride comprises crystalline form D, wherein the tablet comprises an intragranular excipient that comprises of mannitol, croscarmellose sodium, and hypromellose, wherein the amount of mannitol employed in the intragranular excipient mixture is from about 13.5 to about 14.5 percent by weight of the tablet, the amount of croscarmellose sodium employed in the intragranular excipient mixture is from about 2 to about 3 percent by weight of the tablet, and the amount of hypromellose employed in the intragranular excipient mixture is from about 2.5 to about 3.5 percent by weight of the tablet.

In another embodiment, this invention provides a pharmaceutically acceptable tablet comprising ezatiostat hydrochloride, an intragranular excipient, and extragranular excipient, wherein the ezatiostat hydrochloride comprises from about 75 to about 82 percent by weight of the tablet and the ezatiostat hydrochloride comprises crystalline form D, wherein the extragranular excipient comprises one or more of croscarmellose sodium and/or magnesium stearate. In a further embodiment, the amount of croscarmellose sodium employed in the extragranular excipient mixture is from about 1.5 to about 3.5 percent by weight of the tablet. In another embodiment, the amount of magnesium stearate employed in the extragranular excipient mixture is from about 0.5 to about 1.5 percent by weight of the tablet.

In another embodiment, this invention provides a pharmaceutically acceptable tablet comprising ezatiostat hydrochloride, an intragranular excipient, and extragranular excipient, wherein the ezatiostat hydrochloride comprises from about 75 to about 82 percent by weight of the tablet and the ezatiostat hydrochloride comprises crystalline form D, wherein the extragranular excipient is selected from one or more of croscarmellose sodium and magnesium stearate, wherein the amount of croscarmellose sodium employed in the extragranular excipient mixture is from about 2 to about 3 percent by weight of the tablet and the amount of magnesium stearate is about 1 percent by weight of the tablet.

In another embodiment, this invention provides a pharmaceutically acceptable tablet comprising ezatiostat hydrochloride, an intragranular excipient and extragranular excipient wherein the ezatiostat hydrochloride comprises from about 75 to about 82 percent by weight of the tablet and the ezatiostat hydrochloride comprises crystalline form D, wherein said tablet further comprises a film coating.

In another embodiment, this invention provides a pharmaceutically acceptable tablet comprising ezatiostat hydrochloride, an intragranular excipient and extragranular excipient wherein the ezatiostat hydrochloride comprises from about 75 to about 82 percent by weight of the tablet and the ezatiostat hydrochloride comprises crystalline form D, wherein said tablet comprises about 500 mg of ezatiostat hydrochloride. In another embodiment, the tablet comprises preferably about 750 mg, more preferably about 1 gm, and even more preferably about 1.25 gm of ezatiostat hydrochloride.

In another embodiment, this invention provides a pharmaceutically acceptable tablet comprising ezatiostat hydrochloride, an intragranular excipient and extragranular excipient wherein the ezatiostat hydrochloride comprises from about 75 to about 82 percent by weight of the tablet and the ezatiostat hydrochloride comprises crystalline form D, wherein said tablet is stored in a container with a desiccant.

In one of its method embodiments, this invention provides a method of preparing the solid crystalline ansolvate form D.

In another of its method embodiments, this invention provides a method of storing crystalline ezatiostat hydrochloride ansolvate such that the morphology of form D remains stable over its shelf-life and, indeed, for prolonged periods of time. In one aspect of this method, the crystalline ezatiostat hydrochloride ansolvate in an anhydrous environment (e.g., by using desiccants or vacuum conditions to maintain an anhydrous environment).

Identifying The Ansolvate Form D

A solid form screen was carried out on ezatiostat hydrochloride, starting with ezatiostat hydrochloride monohydrate form A, which was previously known. Both thermodynamic and kinetic crystallization techniques were employed. Once solid samples were harvested from crystallization attempts, they were examined under a microscope for birefringence and morphology. The solid samples were characterized by various techniques including those described above. A number of different crystallization techniques were used as set forth below.

Fast evaporation: solutions were prepared in various solvents and sonicated between aliquot additions to assist in dissolution. Once a mixture reached complete dissolution, as judged by visual observation, the solution was filtered through a 0.2 µm nylon filter. The filtered solution was allowed to evaporate at room temperature in an open vial, and the solids that formed were isolated by filtration and dried.

Slow evaporation: solutions were prepared as for the fast evaporation technique above, and the filtered solution was allowed to evaporate at room temperature in a vial covered with aluminum foil perforated with pinholes. The solids that formed were isolated by filtration and dried.

Slow cooling: saturated solutions were prepared in various solvents at elevated temperatures and filtered through a 0.2 µm nylon filter into an open vial while still warm. The vial was covered and allowed to cool slowly to room temperature, and the presence or absence of solids was noted. If there were no solids present, or if the amount of solids was judged too small for XRPD analysis, the vial was placed in a refrigerator overnight. Again, the presence or absence of solids was noted and if there were none, the vial was placed in a freezer overnight. Solids that formed were isolated by filtration and dried.

Crash cooling: saturated solutions were prepared in various solvents or solvent systems at an elevated temperature and filtered through a 0.2-µm nylon filter into an open vial while still warm. The vial was covered and placed directly into a freezer. The presence or absence of solids was noted. Solids that formed were isolated by filtration and dried.

Antisolvent crystallization: solutions were prepared in various solvents at elevated temperature and filtered through a 0.2-µm nylon filter. Solid formation was induced by adding the filtered solution to an appropriate anti-solvent at a temperature below room temperature. The resulting solids were isolated by filtration and dried.

Slurrying: slurries were prepared by adding enough solids to a given solvent so that undissolved solids were present. The mixture was then agitated in a sealed vial at a chosen temperature. After time, the solids were isolated by filtration and dried.

Stress experiments: solids were stressed under different temperature and/or relative humidity (RH) environments for a measured time period. Specific RH values were achieved by placing the sample inside sealed chambers containing saturated salt solutions. Samples were analyzed by XRPD immediately after removal from the stress environment.

In addition to the starting material identified as form A, five additional solid forms were identified. Of the five additional forms, only one, form D, was confirmed to have an unsolvated structure, crystalline ezatiostat hydrochloride ansolvate. The other four forms were determined to be either hydrates, other solvates, or unstable forms.

Ansolvate Form D and its Properties

In one embodiment, this invention provides a crystalline ezatiostat salt ansolvate and, in particular, the hydrochloride ansolvate (crystalline form D). In another embodiment, this invention provides a composition comprising the crystalline ezatiostat hydrochloride ansolvate. Preferably, the crystalline form D is substantially free of a solvated polymorph of ezatiostat hydrochloride. "Substantially free" of a solvated polymorph of ezatiostat hydrochloride refers to a crystalline form D, which excludes solvated polymorph of ezatiostat hydrochloride to an extent that the form D crystals are suitable for human administration. In one embodiment, the crystalline form D contains up to about 5%, more preferably about 3%, and still more preferably about 1% of one or more solvated polymorph of ezatiostat hydrochloride. As used herein, solvate includes hydrate form as well.

It is possible to attain the ansolvate form D with such high polymorphic purity due, in part, to the surprising stability of the ansolvate, and its resistance to conversion to a solvate form, even when stored at 40° C. and 75% RH without a desiccant for 6 months. See Table 5 below. In contrast, the solvate form E transforms almost entirely to form B crystals merely during tablet manufacture, which then transforms into a mixture of form B and the ansolvate form D within 3 months of storage at 40° C. and 75% RH without a desiccant. See Table 6 below. The solvate form A is also polymorphically unstable, converting into a mixture of forms A and D during manufacture. See Table 7 below.

Not only was the ansolvate form D polymorphically stable, it was also more stable to chemical degradation compared to the polymorphs A, B, and E. See Tables 5-7 below in rows entitled "Total impurities." Polymorphic form B, obtained from form E during tablet manufacture, was the most unstable, decomposing at more than double the rate of decomposition of the ansolvate form D. The stability of form D was enhanced even more, when stored in presence of a desiccant. Thus, in another embodiment, the present invention provides a crystalline ansolvate form D, which, when exposed to a temperature of about 25° C. for up to about 6 months in the presence of a desiccant, does not show substantial formation of an impurity. As used herein, "in the presence of a desiccant" refers to the desiccant being placed in a closed container with the ansolvate form D. The closed container, may be, but need not be sealed such that the air from the surrounding can not enter the closed container.

As used herein, "impurity" refers to one or more of: TLK 236, another polymorphic form of ezatiostat hydrochloride including without limitation form A, B, C, E, or F, and any other compound other than ezatiostat hydrochloride ansolvate, which may be identified by HPLC. TLK 236 is a monoester derived from the partial hydrolysis of ezatiostat where the phenyl glycine moiety remains esterified. "Does not show substantial formation of an impurity" refers to formation of only up to about 1.5% or more preferably up to about 1% of impurity.

The crystal form D is desirable from yet another standpoint, which is that, surprisingly, no other ansolvate form being identified upon screening, the ansolvate form D can not convert to another ansolvate polymorph upon storage or handling. And, as described above, ansolvate form D is stable with respect to a conversion to a solvate form, such as A, B, or E.

In another aspect, the present invention provides a method of storing comprising storing the crystalline ezatiostat hydrochloride ansolvate form D in the presence of a desiccant. In one embodiment, the desiccant is amorphous silicate. In another embodiment, the desiccant is Sorb-It silica gel. In one embodiment, the ansolvate form D is stored for up to 3 months, up to 6 months, up to 9 months, up to 1 year, up to 1.5 years, up to 2 years, up to 3 years, or up to 4 years. In another embodiment, the ansolvate form D is stored at a temperature of up to about 5° C. In another embodiment, the ansolvate form D is stored at a temperature of up to about 25° C. In another embodiment, the ansolvate form D is stored at a temperature of up to about 40° C.

Furthermore, as part of a tablet, the ansolvate form D demonstrated higher aqueous dissolution rate than polymorphic form E (which converts to form B upon tableting) or B, when measured in 0.1 molar HCl, which is a convenient model for gastric fluid. Without being bound by theory, a higher dissolution rate relates to a higher amount of the active agent in the gastric fluid, which in turn relates to higher bioavailability of the active agent. A high bioavailability is desired, for example and without limitation, for reducing inter patient variability of drug exposure for a orally administered agent such as ezatiostat hydrochloride. So, for therapeutic use, the ansolvate form D is contemplated to be advantageous over form B or E. In one embodiment, the present invention provides a composition including the crystalline form D, which shows an aqueous solubility of at least about 5 mg/mL to about 20 mg/mL, about 10 mg/mL to about 15 mg/mL, about 5 mg/mL to about 15 mg/mL, or about 15 mg/mL to about 20 mg/mL. The aqueous solubility can be measured in a variety of aqueous solvents, including without limitation, water, 0.9% aqueous NaCl, 5% dextrose for injection, phosphate buffered saline, and generally aqueous solutions having a pH of less than about 5. Such solvents may include suitable buffers and other salts.

Preparation of Ansolvate Form D

In another aspect, this invention provides a method of preparing the solid crystalline ansolvate provided herein. In one embodiment, the method comprises slurrying ezatiostat hydrochloride in methyl tert-butyl ether at room temperature. In another embodiment, the method comprises slurrying ezatiostat hydrochloride in hexanes at about 60° C. In another embodiment, the method comprises heating ezatiostat hydrochloride monohydrate form A at a temperature from above about 155° C. up to less than the decomposition temperature and preferably to no more than about 180° C. for a period sufficient to convert the monohydrate to the ansolvate form D. Based on the present disclosure such transformations can be readily performed by the skilled artisan, for example, by monitoring DSC results.

In still another aspect, ezatiostat hydrochloride ansolvate is also obtained by dissolution of crude hydrated ezatiostat hydrochloride in about 5.6 times its weight of ethanol, heating to about (65-70)° C., filtering, seeding with a small quantity (e.g. about 2% by weight of the initial ezatiostat hydrochloride) of ezatiostat hydrochloride ansolvate, cooling to about 40° C., adding ethyl acetate in about 13.5 times the weight of the ezatiostat hydrochloride ansolvate, gradually cooling to about (20-25)° C. and then to (−5-0)° C., then filtering, washing with ethyl acetate, and drying.

Characterization of Crystalline Forms of Ezatiostat Hydrochloride

Crystalline ezatiostat hydrochloride ansolvate is characterized by its chemical composition, i.e. the presence of ezatiostat hydrochloride and the absence of water or other solvents of crystallization, and the crystalline nature of the material (the presence of an XRPD pattern characteristic of a crystalline, as opposed to amorphous, material). It may further conveniently be characterized by methods such as DSC, XRPD, and SS-NMR. It may also be characterized by other methods. These include analysis for water determination (typically by Karl Fischer analysis), where none or only a small quantity of water—significantly less than that which would be expected from a hydrate such as the monohydrate—should be found; and TG or TG-IR analysis, where none or only a small weight loss—significantly less than that which would be expected by the loss of a solvent of crystallization—would be found.

By DSC, crystalline ezatiostat hydrochloride ansolvate is characterized by an endothermic peak at (177±2)° C., which corresponds to melting of the crystalline ezatiostat hydrochloride ansolvate. If the crystalline ezatiostat hydrochloride ansolvate is free of other forms of ezatiostat hydrochloride, the DSC pattern will be characterized also by the substantial absence of thermal events at temperatures below the endothermic peak at (177±2)° C.; but the presence of minor quantities of other forms such as ezatiostat hydrochloride monohydrate will result in the presence of minor thermal events at lower temperatures. As used herein, "substantial absence of thermal events" refer to endotherms and exotherms related to melting and recrystallization.

Figure 6:
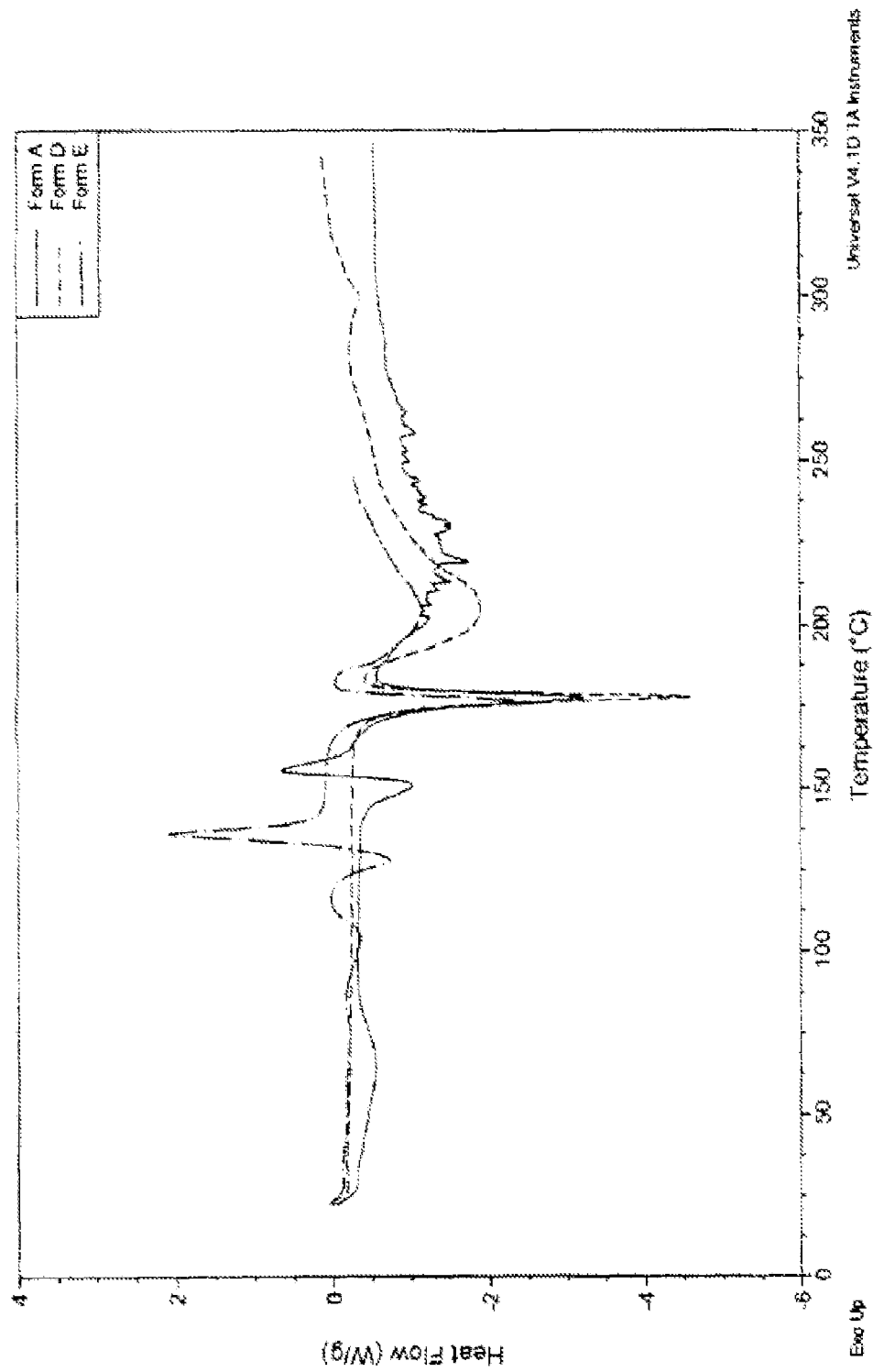
FIG. 6 is a comparative DSC pattern of crystalline ezatiostat hydrochloride polymorphic forms A, D, and E.

In one embodiment, this invention provides a tablet comprising a crystalline ansolvate form D characterized by an endothermic peak at (177±2)° C. as measured by differential scanning calorimetry (DSC). In another embodiment, this invention provides a tablet comprising a crystalline ansolvate form D characterized by substantial absence of thermal events at temperatures below the endothermic peak at (177±2)° C. as measured by differential scanning calorimetry. See, FIG. 6, which graphically illustrates a comparative DSC of forms A, D, and E, and demonstrates substantial absence of thermal events at temperatures below the endothermic peak at (177±2)° C. for the crystalline ansolvate form D.

Under XRPD, crystalline ezatiostat hydrochloride ansolvate is characterized by a dominant zone with a rectangular planar (2-dimensional) unit cell with axial lengths of about 18.28 Å and 64.23 Å and an included angle of 90°; and systematic extinctions indicating that the planar cell has p2gg symmetry. Only two 3-dimensional space groups are consistent with the observed dominant zone cell and an ordered packing of a single diastereomer of a chiral molecule: these are orthorhombic space groups ($P2_12_12$ or $P2_12_12_1$) with approximate unit cell dimensions of a=64.23 Å, b=18.28 Å, c=short ($P2_12_12$), or a=short, b=18.28 Å, c=64.23 Å ($P2_12_12_1$). Note that permutations of the a and b axes are permissible for $P2_12_12$, and of all three axes for $P2_12_12_1$. The lowest-angle feature not related to the dominant zone is near 17.5° 2θ, indicating a short axis of about 5.1 Å (best match indexing solutions are consistent with about 5.08 Å, but there is insufficient peak resolution above 17° 2θ to definitively determine the length of the short axis and the space group). XRPD patterns will show peaks characteristic of this unit cell, as discussed further in the Examples below.

In another embodiment, this invention provides a tablet comprising a crystalline ansolvate form D characterized by at least one X-ray powder diffraction peak (Cu Kα radiation) selected from 2.7°, 6.3°, 7.3°, 8.2°, 8.4°, 9.6°, 11.0°, and 12.7° 2θ (each ±0.2° 2θ). In another embodiment, this invention provides a crystalline ansolvate form D characterized by an X-ray powder diffraction peak (Cu Kα radiation) at (2.7±0.2)° 2θ. In another embodiment, this invention provides a tablet comprising a crystalline ansolvate form D characterized by an X-ray powder diffraction peak (Cu Kα radiation) at (6.3±0.2)° 2θ. In another embodiment, this invention provides a tablet comprising a crystalline ansolvate form D characterized by at least two X-ray powder diffraction peaks (Cu Kα radiation) selected from 2.7°, 6.3°, 7.3°, 8.2°, 8.4°, 9.6°, 11.0°, and 12.7° 2θ (each ±0.2° 2θ). In another embodiment, this invention provides a tablet comprising a crystalline ansolvate form D characterized by at least three X-ray powder diffraction peaks (Cu Kα radiation) selected from 2.7°, 6.3°, 7.3°, 8.2°, 8.4°, 9.6°, 11.0°, and 12.7° 2θ (each ±0.2° 2θ). In another embodiment, this invention provides a tablet comprising a crystalline ansolvate form D characterized by at least one X-ray powder diffraction peak (Cu Kα radiation) selected from 2.7°, 6.3°, 7.3°, 8.2°, 8.4°, 9.6°, 11.0°, and 12.7° 2θ (each ±0.2° 2θ).

Figure 3:
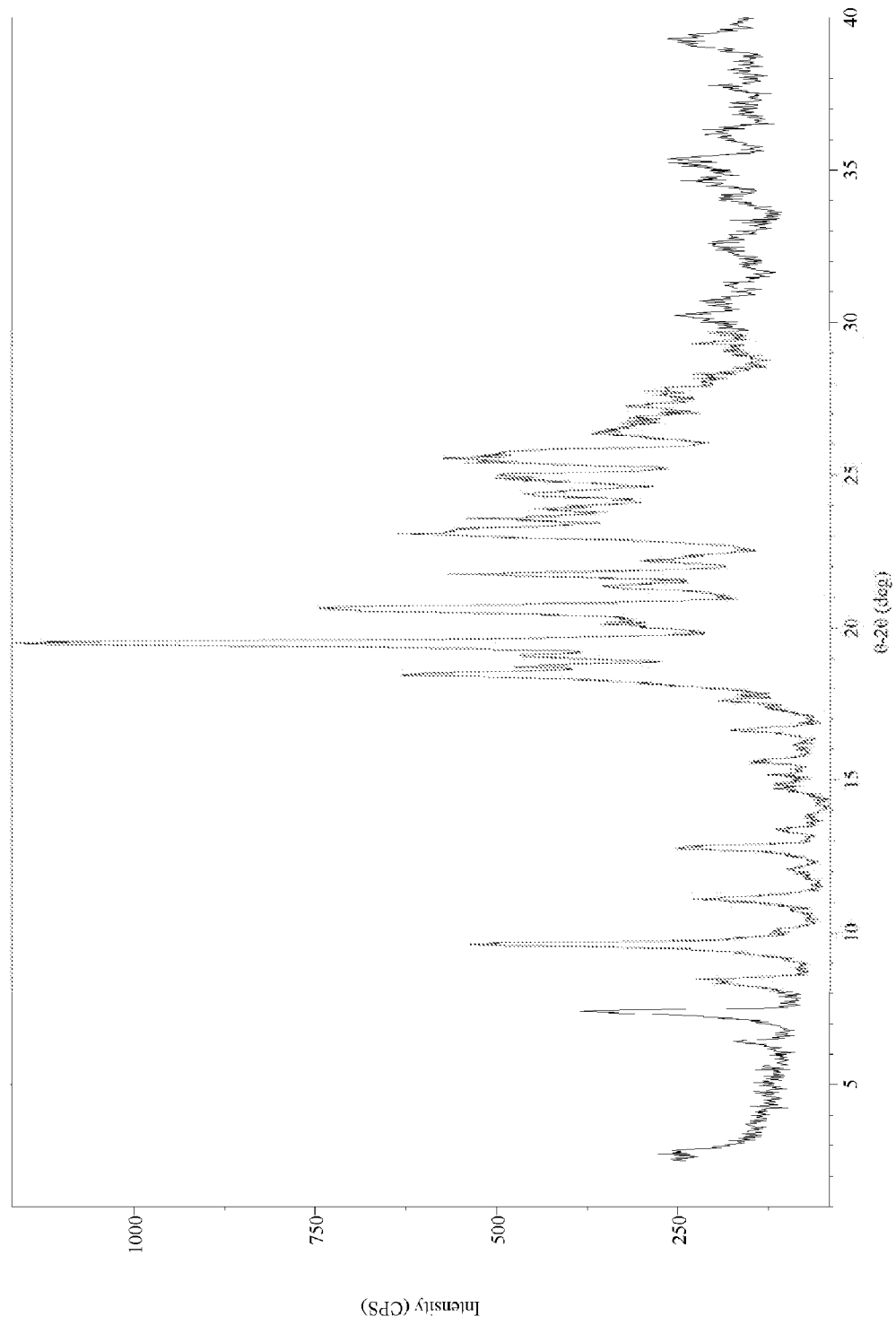
FIG. 3 is an XRPD pattern of crystalline ezatiostat hydrochloride ansolvate form D.
Figure 4:
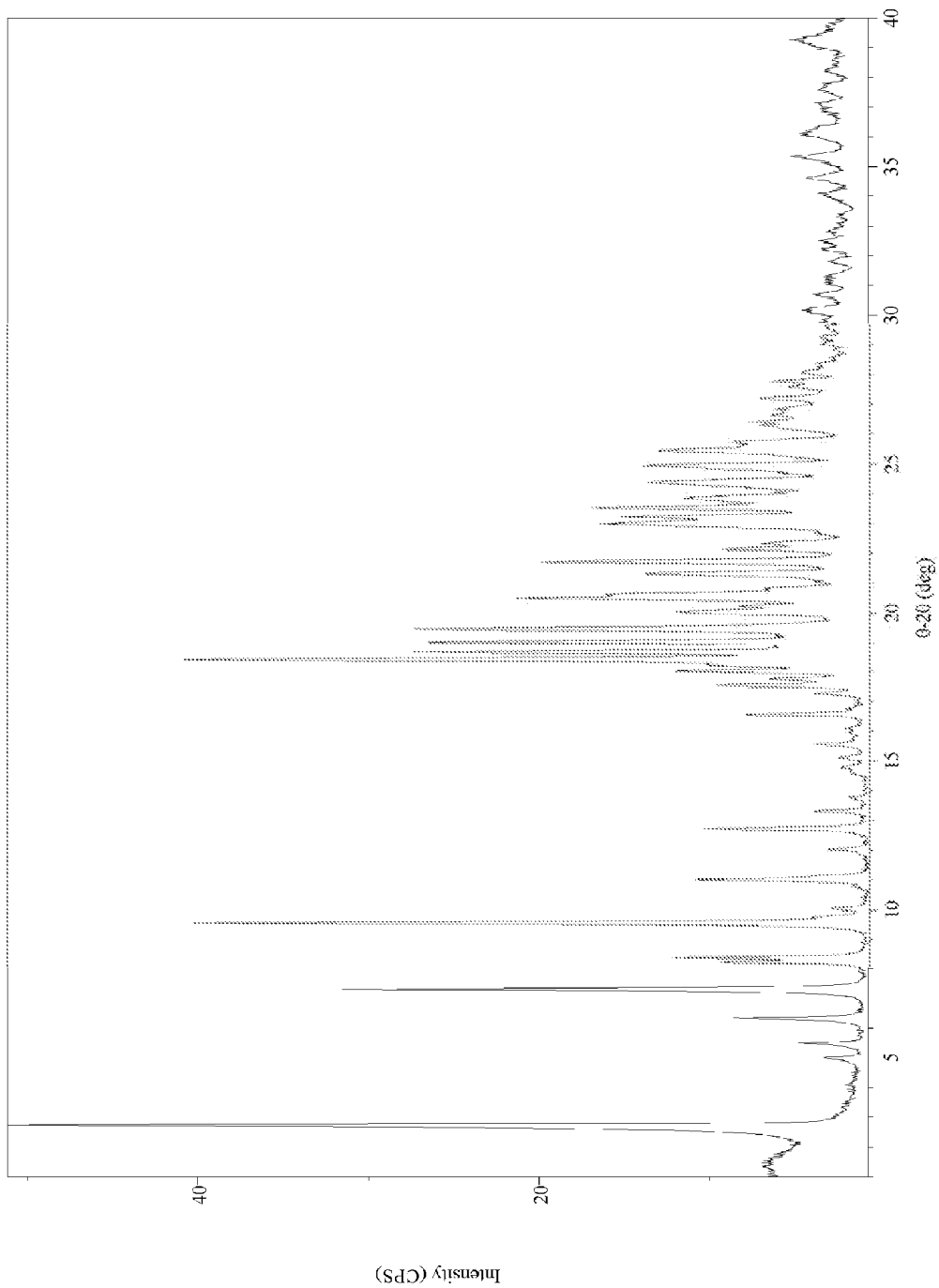
FIG. 4 is a high-resolution XRPD pattern of crystalline ezatiostat hydrochloride ansolvate form D.

In another embodiment, this invention provides a tablet comprising a crystalline ansolvate form D characterized by an X-ray powder diffraction pattern (Cu Kα radiation) substantially similar to that of FIG. 3 or FIG. 4. In another embodiment, this invention provides a tablet comprising a crystalline ansolvate form D characterized by a solid-state $^{13}C$ nuclear magnetic resonance spectrum substantially similar to that of FIG. 5.

Methods of therapeutic uses of ezatiostat are disclosed in U.S. Provisional Patent Application 61/352,371, 61/352,373, and 61/352,374, each of which was filed on Jun. 7, 2010; the contents of which are incorporated herein by reference in their entirety.

It will be apparent to those skilled in the art that many modifications of the above examples, both to materials and methods, may be practiced without departing from the scope of the current invention.

EXAMPLES

The following examples describe the preparation of a tablet comprising ezatiostat hydrochloride, as well as the preparation, characterization, and properties of ezatiostat hydrochloride ansolvate. Unless otherwise stated, all temperatures are in degrees Celcius (° C.) and the following abbreviations have the following definitions:

DSC=Differential scanning calorimetry
NA=Not applicable
Q=Percent dissolved per unit time
RH=Relative humidity
RSD=Relative standard deviation
RRT=Relative retention time
SS-NMR=Solid state nuclear magnetic resonance
TG-IR=Thermogravimetric infra red analysis
XRPD=X-ray powder diffraction
VT-XRPD=Variable temperature X-ray powder diffraction

Example 1

Formulations of Ezatiostat Hydrochloride

Two different formulations comprising ezatiostat hydrochloride were prepared by mixing ezatiostat hydrochloride with the each of the excipient mixtures 1 and 2 in a 3.3:1 ratio. Specifically, formulation 1 was prepared by mixing 75 mg of excipient mixture 1 with 250 mg of ezatiostat hydrochloride, whereas formulation 2 was prepared by mixing 75 mg of excipient mixture 2 with 250 mg of ezatiostat hydrochloride. Table 3 provides the different ingredients used in the excipient mixtures 1 and 2.

TABLE 3

Excipient mixtures for ezatiostat hydrochloride formulations

| Ingredient | Excipient mixture 1 (mg) | Excipient mixture 2 (mg) |
|---|---|---|
| Microcrystalline cellulose (Avicel PH 112) | 88.25 | |
| Mannitol granular (Mannogem granular 2080) | | 88.25 |
| Croscarmellose sodium | 32.5 | |
| Crospovidone | | 32.5 |
| Providone K-29/32 | | 19.5 |
| HPMC E5 Premium | 19.5 | |
| Colloidal silicon dioxide | 3.25 | 3.25 |
| Magnesium stearate | 6.5 | 6.5 |

Example 2

General Process for Preparing a Tablet comprising Ezatiostat Hydrochloride

The required amounts of Ezatiostat hydrochloride, mannitol, croscarmellose sodium and hypromellose were dispensed and milled as necessary. The mixture was then dry blended in a high shear granulator. Adequate amount of purified water was added and the mixture was then granulated. The granulate was wet screened and dried in a fluid bed dryer. The dried granules were milled and the granulate was then blended with adequate amount of croscarmellose sodium in a V blender. Then the mixture was blended with magnesium stearate in a V blender. The blend was compressed into tablets and coated with an Opadry® Clear solution. The coated tablets were dispensed into bottles, induction seal was applied, and the bottles were capped and labeled. Table 4 shows the various parameters for four different lots of the tablet.

TABLE 4

Compression Parameters for the tablet

| Parameter | | Drug Product Lot Number | | | |
|---|---|---|---|---|---|
| | | 1 | 2 | 3 | 4 |
| Compression pressure (kN) | | 7.1 | 15.5 | 13.2 | 13.5 |
| Tablet Weight Target: 650 mg | Mean | 654.2 | 652.5 | 655.8 | 653.2 |
| | Range | 624-681 | 645-659 | 651-665 | 648-660 |
| | Mean | 654.0 | 653.2 | 651.1 | 651.5 |
| Range: 618-683 mg | Range | 628-682 | 650-657 | 648-655 | 648-655 |
| | Mean | 652.2 | 653.2 | 651.8 | 651.2 |
| | Range | 635-667 | 649-657 | 647-657 | 648-654 |
| Tablet Hardness Target: | Mean | 11.1 | 11.5 | 12.1 | 13.0 |
| | Range | 8.3-15.3 | 10.6-12.0 | 10.7-13.8 | 11.0-14.3 |
| | Mean | 11.3 | 10.6 | 10.5 | 11.4 |

TABLE 4-continued

Compression Parameters for the tablet

| Parameter | | Drug Product Lot Number | | | |
|---|---|---|---|---|---|
| | | 1 | 2 | 3 | 4 |
| 12 kP Range: | Range | 9.3-12.5 | 9.6-11.0 | 9.8-11.3 | 10.5-12.5 |
| | Mean | 11.4 | 10.5 | 11.3 | 12.3 |
| 8-16 kP | Range | 9.2-13.6 | 10.2-11.0 | 10.6-12.2 | 10.5-13.3 |
| Tablet Thickness Target: | Mean | 6.47 | 5.95 | 6.04 | 6.08 |
| | Range | 6.32-6.61 | 5.92-6.05 | 6.00-6.07 | 6.04-6.20 |
| | Mean | 6.45 | 5.95 | 6.02 | 6.09 |
| 6.50 mm Range: | Range | 6.39-6.53 | 5.94-5.97 | 5.99-6.10 | 6.07-6.11 |
| | Mean | 6.41 | 5.95 | 5.96 | 6.01 |
| 5.50-7.00 mm | Range | 6.38-6.50 | 5.92-6.00 | 5.94-5.99 | 5.99-6.02 |
| Friability Spec: NMT 0.8% | Begin. | 0.2% | 0.2% | 0.2% | 0.2% |
| | End | 0.2% | 0.2% | 0.3% | 0.2% |
| Disintegration Spec.: NMT 15 min. | Begin. | 0:02:34 | 0:09:53 | 0:08:23 | 0:07:15 |
| | End | 0:02:48 | 0:10:50 | 0:11:46 | 0:07:48 |

Example 3

Preparation of Ezatiostat Hydrochloride Ansolvate by Slurrying

Ezatiostat hydrochloride monohydrate was added to methyl tert-butyl ether at room temperature in excess, so that undissolved solids were present. The mixture was then agitated in a sealed vial at room temperature for 4 days, and the solids were then isolated by suction filtration. XRPD analysis of the solids established that the isolated solids were ezatiostat hydrochloride ansolvate.

Ezatiostat hydrochloride monohydrate was added to hexanes at 60° C. in excess, so that undissolved solids were present. The mixture was then agitated in a sealed vial at 60° C. for 4 days, and the solids were then isolated by suction filtration. XRPD analysis of the solids established that the isolated solids were ezatiostat hydrochloride ansolvate.

Example 4

Preparation of Crystalline Ezatiostat Hydrochloride Ansolvate by Heating

Figure 2:
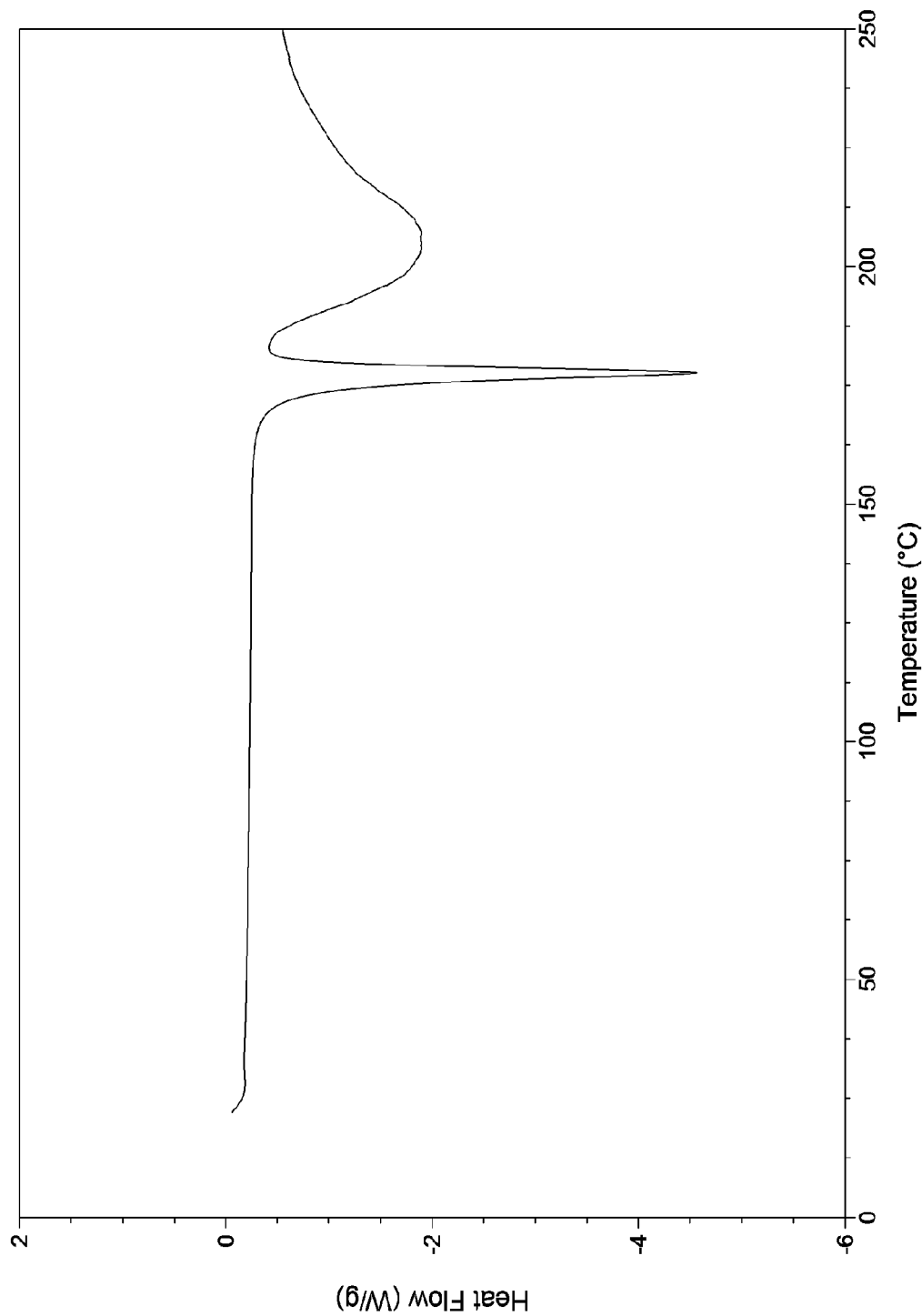
FIG. 2 is a DSC pattern of crystalline ezatiostat hydrochloride ansolvate form D.

DSC of crystalline ezatiostat hydrochloride monohydrate showed the pattern in FIG. 1, as discussed in paragraph above. Hot stage microscopy showed an initial melt followed by a recrystallization at 153° C. and a final melt at 166° C. VT-XRPD, where XRPD patterns were obtained at 28° C., 90° C., and 160° C. during heating, and 28° C. after cooling of the formerly heated material, showed the presence of ezatiostat hydrochloride monohydrate at 28° C. and 90° C. during heating and of crystalline ezatiostat hydrochloride ansolvate at 160° C. and 28° C. after cooling of the formerly heated material. This confirmed that the transition at around 153/156° C. was a conversion of ezatiostat hydrochloride monohydrate form A to crystalline ezatiostat hydrochloride ansolvate form D and that the final DSC endothermic peak at about 177° C. (166° C. in the hot stage microscopy) was due to the melting of crystalline ezatiostat hydrochloride ansolvate. This was further confirmed by XRPD of the TG-IR material, where XRPD patterns obtained at room temperature both before and after heating to about 160° C. showed that the material before heating was form A and that the material after heating was form D ansolvate. DSC of crystalline ezatiostat hydrochloride ansolvate prepared by recrystallization showed the pattern in FIG. 2, with only the endothermic peak at about 177° C. followed by a broad endotherm at about (205-215)° C. Accordingly, the presence of the DSC endothermic peak at about 177° C., for example at (177±2)° C., when measured under the conditions described above, is considered characteristic of crystalline ezatiostat hydrochloride ansolvate, and the substantial absence of thermal events at temperatures below this is considered indicative of the absence of other forms of ezatiostat hydrochloride.

Example 5

Preparation of Crystalline Ezatiostat Hydrochloride Ansolvate by Crystallization 61.5 Kg crude ezatiostat hydrochloride was added to a reactor at room temperature, followed by 399 liter (L) ethanol, and this mixture was heated to 68° C. to completely dissolve the ezatiostat hydrochloride, filtered, then allowed to cool to 65° C. and checked for clarity and the absence of crystallization. About 1.3 Kg of ezatiostat hydrochloride ansolvate form D was suspended in 9 L of ethyl acetate, and about one-half of this suspension was added to the ethanol solution. The mixture was cooled to 63° C. and the second half of the suspension added to the mixture. The resulting mixture was cooled gradually to 45° C., 928 L ethyl acetate was added, and the mixture was cooled to 26° C. and held at about that temperature for about 5 hours, then cooled to −2° C. The mixture, containing crystalline ezatiostat hydrochloride ansolvate, was filtered, and the residue washed twice with 65 L of chilled (0-5° C.) ethyl acetate. The crystalline ezatiostat hydrochloride ansolvate was dried at 30° C. for 48 hours, then cooled to room temperature and sieved. Analysis of the material by DSC and XRPD confirmed its identity as crystalline ezatiostat hydrochloride ansolvate, and Karl Fischer analysis showed a water content of 0.1%.

XRPD of form D showed the pattern in FIG. 3. High-resolution XRPD of form D showed the pattern in FIG. 4. The major peaks are at 2.7°, 5.0°, 5.5°, 6.3°, 7.3°, 8.2°, 8.4°, 9.6°, 10.1°, 11.0°, 12.0°, 12.7°, 13.3°, 13.8°, 14.8°, 15.1°, 15.6°, 16.1°, 16.6°, 17.3°, 17.5°, 17.8°, 18.0°, 18.4°, 18.7°, 19.0°, 19.5°, 20.0°, 20.5°, 21.3°, 21.7°, 22.1°, 22.3°, 23.0°, 23.2°, 23.5°, 23.8°, 24.4°, 24.9°, 25.4°, 25.7°, 26.4°, 26.7°, 27.2°, 27.6°, 27.8°, 28.0°, and 29.3° 2θ. These peaks listed here at less than about 15° 2θ exhibit good separation from each other and are easily discernable even at lower resolution. Low angle peaks such as the peaks at 2.7°, 6.3°, 7.3°, 8.2°, 8.4°, 9.6°, 11.0°, and 12.7° 2θ are particularly useful in characterization of crystalline ezatiostat hydrochloride ansolvate; and at least one, preferably at least two, more preferably at least three of these peaks may be used. In particular, the peaks at 2.7° and 7.3° 2θ, especially the peak at 2.7° 2θ, may be considered characteristic of crystalline ezatiostat hydrochloride ansolvate.

Figure 5:
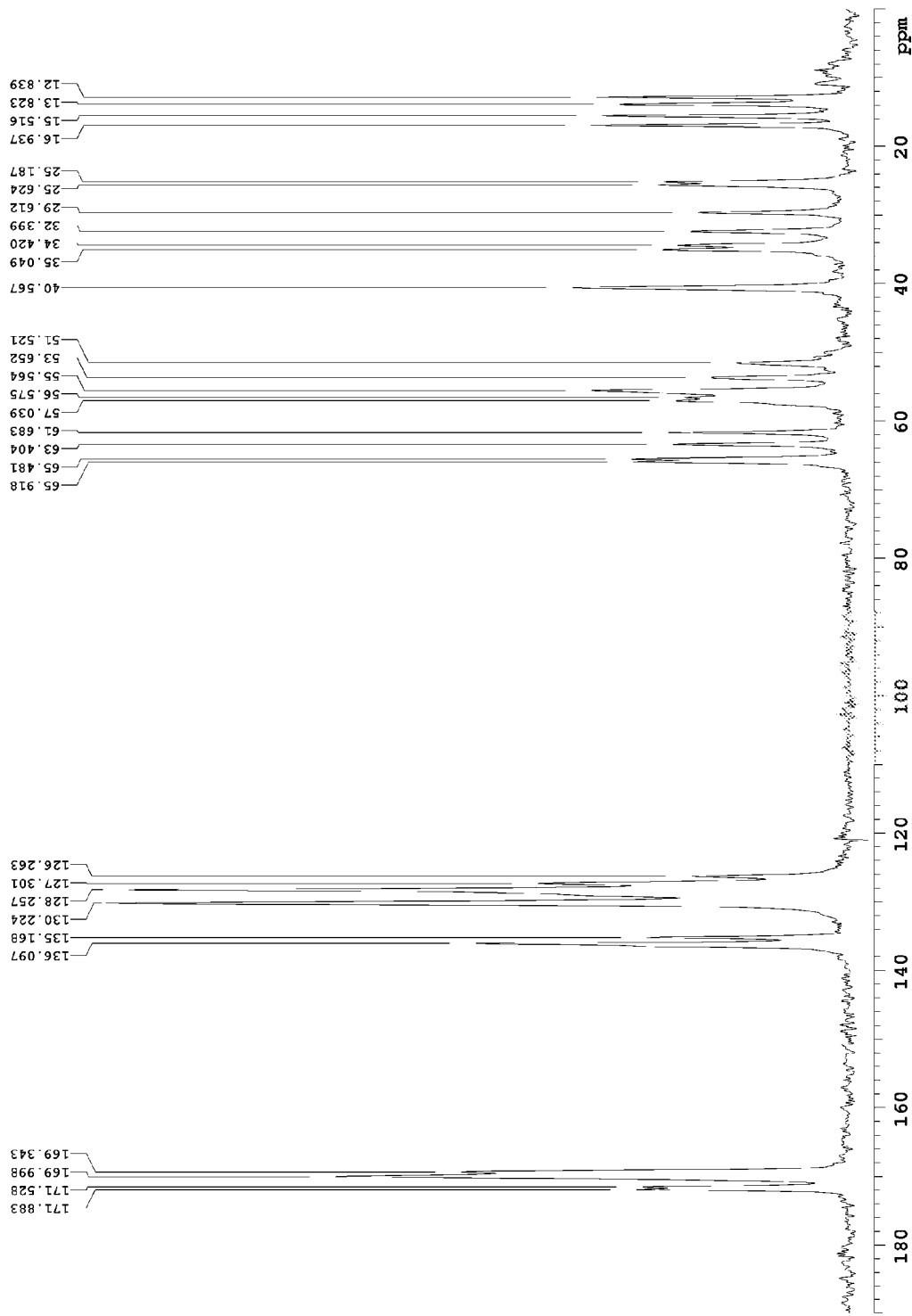
FIG. 5 is an SS-NMR spectrum of crystalline ezatiostat hydrochloride ansolvate form D.

SS-NMR analysis of crystalline ezatiostat hydrochloride ansolvate showed the pattern in FIG. 5, clearly distinguishable from that of ezatiostat hydrochloride monohydrate.

In summary, crystalline ezatiostat hydrochloride ansolvate form D is characterized by chemical composition, i.e. the presence of ezatiostat hydrochloride and the absence of water or other solvents of crystallization, and the crystalline nature of the material (the presence of an XRPD pattern characteristic of a crystalline, as opposed to amorphous, material). Additionally, the presence of the DSC endothermic peak at (177±2)° C. alone, or the presence of one or more of the low angle XRPD peaks (especially the peak at 2.7° 2θ, alone or with one or more of the other peaks below 15° 2θ, such as the peaks at 6.3°, 7.3°, 8.2°, 8.4°, 9.6°, 11.0°, and 12.7° 2θ, especially such as the peak at 7.3° 2θ and optionally one or more of the other peaks listed), preferably also in the absence of peaks indicative of ezatiostat hydrochloride monohydrate or other forms of ezatiostat hydrochloride, are considered characteristic of crystalline ezatiostat hydrochloride ansolvate. Also considered characteristic of crystalline ezatiostat hydrochloride ansolvate is XRPD patterns substantially the same as those in FIG. 3 or FIG. 4, when measured under the conditions described above.

Example 6

Polymorphic and Physicochemical Stability of Form D Ansolvate in the Absence of Desiccants This example demonstrates the superior stability and solubility of the ansolvate form D compared to the solvate forms A, B, and E. Tablets of forms A, D, and E were made and stored at 40° C./75% RH without a desiccant for up to 6 months and the various properties of the tablets determined initially, and at 3 and 6 month intervals. As described above, form E converts to form B simply during tableting. The results are tabulated below.

TABLE 5

Polymorphic and Physicochemical Stability of Form D Ansolvate in the Absence of Desiccants when stored at 40° C./75% RH

| API Polymorph Form | | Polymorph Form D | | |
|---|---|---|---|---|
| Timepoint | | Initial | 3 Month | 6 Month |
| Description | White to off-white round tablet | White round tablet | Off-white round tablet | Brown round tablet |
| Assay (HPLC) | 93.0-107.0% Label Claim | 101.4 | 100.3 | 96.5 |
| Dissolution | Q = 70% of label claim dissolved in 45 min | At 45 min, individual results: 37, 50, 32, 73, 54, 57 Mean = 51 RSD % = 29.1 | At 45 min, individual results: 95, 93, 96, 67, 98, 81 Mean = 88 RSD % = 13.6 | At 45 min, individual results: 68, 95, 73, 80, 71, 100 Mean = 81 RSD % = 16.3 |
| Water Content | ≦5.0% | 0.9 | 0.8 | 0.8 |
| X-ray Diffraction | Report results | Polymorph D | Polymorph D | Polymorph D |

TABLE 5-continued

Polymorphic and Physicochemical Stability of Form D Ansolvate in the Absence of Desiccants when stored at 40° C./75% RH

| API Polymorph Form | | Polymorph Form D | | |
|---|---|---|---|---|
| Timepoint | | Initial | 3 Month | 6 Month |
| Individual Impurities | RRT = 0.59/0.62 | ND | ND | 0.08 |
| | RRT = 0.74 | 0.21 | 0.21 | 0.20 |
| | RRT = 0.80 | ND | ND | ND |
| | RRT = 0.81 | ND | ND | ND |
| | RRT = 0.83 | ND | 0.07 | 0.09 |
| | RRT = 0.86 | ND | ND | ND |
| TLK 236 | RRT = 0.88 | 0.35 | 1.33 | 2.07 |
| | RRT = 0.94 | ND | 0.07 | ND |
| | RRT = 0.96 | 0.18 | 0.19 | 0.23 |
| | RRT = 0.99 | ND | ND | ND |
| Total impurities | | 0.7 | 1.9 | 2.7 |

TABLE 6

Polymorphic and Physicochemical Stability of Form E in the Absence of Desiccants when stored at 40° C./75% RH

| API Polymorph Form | | Polymorph Form E | | |
|---|---|---|---|---|
| Timepoint | | Initial | 3 Month | 6 Month |
| Description | White to off-white round tablet | White round tablet | Off-white round tablet | Brown round tablet |
| Assay (HPLC) | 93.0-107.0% Label Claim | 93.7 | 90.3 | 84.6 |
| Dissolution | Q = 70% of label claim dissolved in 45 min | At 45 min, individual results: 47, 49, 43, 45, 47, 47 Mean = 46 RSD % = 4.3 | At 45 min, individual results: 47, 31, 27, 30, 23, 42 Mean = 33 RSD % = 26.9 | At 45 min, individual results: 17, 18, 18, 21, 26, 16 Mean = 19 RSD % = 19.4 |
| Water Content | ≦5.0% | 3.5 | 2.3 | 2.3 |
| X-ray Diffraction | Report results | Polymorph B | Polymorph B and D | Polymorph B and D |
| Individual Impurities | RRT = 0.59/0.62 | ND | 0.07 | 0.15 |
| | RRT = 0.74 | 0.38 | 0.42 | 0.51 |
| | RRT = 0.80 | ND | 0.16 | 0.41 |
| | RRT = 0.81 | ND | 0.14 | 0.17 |
| | RRT = 0.83 | 0.34 | 0.31 | 0.16 |
| | RRT = 0.86 | ND | 0.06 | ND |
| TLK 236 | RRT = 0.88 | 0.42 | 3.45 | 4.66 |
| | RRT = 0.94 | ND | 0.08 | ND |
| | RRT = 0.96 | 0.20 | 0.19 | 0.24 |
| | RRT = 0.99 | 0.12 | 0.20 | ND |
| Total impurities | | 1.5 | 5.1 | 6.3 |

TABLE 7

Polymorphic and Physicochemical Stability of Form A in the Absence of Desiccants when stored at 40° C./75% RH

| API Polymorph Form | | Polymorph Form A | | |
|---|---|---|---|---|
| Timepoint | | Initial | 3 Month | 6 Month |
| Description | White to off-white round tablet | White round tablet | Off-white round tablet | Off-white round tablet |

TABLE 7-continued

Polymorphic and Physicochemical Stability of Form A in the Absence of Desiccants when stored at 40° C./75% RH

| API Polymorph Form | | Polymorph Form A | | |
|---|---|---|---|---|
| Timepoint | | Initial | 3 Month | 6 Month |
| Assay (HPLC) | 93.0-107.0% Label Claim | 97.2 | 94.1 | 91.5 |
| Dissolution | Q = 70% of label claim dissolved in 45 min | At 45 min, individual results: 12, 12, 11, 12, 12, 11 Mean = 12 RSD % = 4.0 | At 45 min, individual results: 88, 49, 64, 81, 77, 83 Mean = 74 RSD % = 19.7 | At 45 min, individual results: 79, 83, 73, 80, 25, 86 Mean = 71 RSD % = 32.5 |
| Water Content | ≦5.0% | 2.1 | 1.7 | 1.9 |
| X-ray Diffraction | Report results | Polymorph A and D | Polymorph A and D | Polymorph A and D |
| Individual Impurities | RRT = 0.59/0.62 | ND | ND | 0.07 |
| | RRT = 0.74 | 0.13 | 0.16 | 0.15 |
| | RRT = 0.80 | ND | 0.08 | 0.14 |
| | RRT = 0.81 | ND | 0.07 | 0.05 |
| | RRT = 0.83 | 0.46 | 0.10 | ND |
| | RRT = 0.86 | ND | ND | ND |
| TLK 236 | RRT = 0.88 | 0.45 | 1.99 | 2.92 |
| | RRT = 0.94 | ND | 0.07 | ND |
| | RRT = 0.96 | 0.16 | 0.16 | 0.21 |
| | RRT = 0.99 | ND | 0.07 | ND |
| Total impurities | | 1.2 | 2.7 | 3.5 |

Example 7

Polymorphic and Physicochemical Stability of Form D Ansolvate in Presence of Desiccants The stability of the ansolvate form D was further improved when stored in presence of a desiccant as demonstrated in this example. Tablets of ansolvate form D, were packaged with and without desiccant (Sorb-It Cannister, 1 gram). Fifty tablets were packaged in a round, white 1500 mL bottle with a screw cap over an induction seal. Impurities were assayed by HPLC. When stored at 25° C./60% RH with desiccant for 3 months, no increase in total impurities was observed. When stored at 40° C./75% RH with desiccant for 3 months, total impurities increased only by 0.3%. When stored at 40° C./75% RH without desiccant for 3 months, total impurities still increased by 1.1%. As tabulated below, the presence of desiccant appears to further increase the stability of the ansolvate form D. Even though the dissolution rate of tablets containing polymorph D from one batch was below specification (<70%) at an initial test as well as after 3 months at 25° C./60% RH with desiccant, the subsequent batches met the required specification.

TABLE 8

Polymorphic and Physicochemical Stability of Form D Ansolvate in Presence of Desiccants

| | | Timepoint | | | |
|---|---|---|---|---|---|
| | | Initial | 3 Month | 3 Month | 3 Month |
| | | | Storage | | |
| | | NA | 40° C./75% RH without desiccant | 25° C./60% RH with desiccant | 40° C./75% RH with desiccant |
| Description | | White to off-white round tablet | White round tablet | Off-white round tablet | White round tablet | Off-white round tablet |
| Assay (HPLC) | 93.0-107.0% Label Claim | 101.4 | 100.3 | 99.7 | 100.8 |
| Dissolution | Q = 70% of label claim dissolved in 45 min | At 45 min, individual results: 37, 50, 32, 73, 54, 57 Mean = 51 RSD % = 29.1 | At 45 min, individual results: 95, 93, 96, 67, 98, 81 Mean = 88 RSD % = 12.0 | At 45 min, individual results: 36, 57, 43, 29, 53, 59 Mean = 46 RSD % = 12.2 | At 45 min, individual results: 87, 52, 84, 97, 77, 59 Mean = 76 RSD % = 17.1 |
| Water Content | ≦5.0% | 0.9 | 0.8 | 0.5 | 0.6 |
| X-ray Diffraction | Report results | Polymorph D | Polymorph D | Polymorph D | Polymorph D |
| Individual | RRT = | 0.21 | 0.18 | 0.16 | 0.16 |

TABLE 8-continued

Polymorphic and Physicochemical Stability of Form D Ansolvate in Presence of Desiccants

| | | Timepoint | | | |
|---|---|---|---|---|---|
| | | Initial | 3 Month | 3 Month | 3 Month |
| | | | Storage | | |
| | | NA | 40° C./75% RH without desiccant | 25° C./60% RH with desiccant | 40° C./75% RH with desiccant |
| Impurities | 0.74/0.72 | | 0.08 | | 0.09 |
| | RRT = 0.83 | ND | | ND | |
| TLK 236 | RRT = 0.88 | 0.35 | 1.3 | 0.34 | 0.53 |
| | RRT = 0.94 | ND | 0.07 | ND | 0.06 |
| | RRT = 0.96 | 0.18 | 0.18 | 0.19 | 0.19 |
| Total impurities | | 0.7 | 1.8 | 0.7 | 1.0 |

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

What is claimed is:

1. A pharmaceutically acceptable tablet comprising a crystalline ansolvate of ezatiostat hydrochloride, an intragranular excipient, and an extragranular excipient, wherein the crystalline ansolvate of ezatiostat hydrochloride comprises from about 75 to about 82 percent by weight of the tablet and wherein the crystalline ansolvate of ezatiostat hydrochloride is form D.

2. The pharmaceutically acceptable tablet of claim 1, wherein said tablet comprises from about 100 mg to about 1250 mg of ezatiostat hydrochloride.

3. The pharmaceutically acceptable tablet of claim 1, wherein the intragranular excipient is selected from the group consisting of mannitol, croscarmellose sodium, and hypromellose.

4. The pharmaceutically acceptable tablet of claim 3, wherein the intragranular excipient comprises a mixture of mannitol, croscarmellose sodium, and hypromellose.

5. The pharmaceutically acceptable tablet of claim 4, wherein the intragranular excipient comprises from about 17 to about 21 percent by weight of the tablet.

6. The pharmaceutically acceptable tablet of claim 5, wherein total amount of the intragranular excipient is from about 19 to about 20 percent by weight of the tablet.

7. The pharmaceutically acceptable tablet of claim 6, wherein the amount of mannitol employed in the intragranular excipient mixture ranges from about 13 to about 15 percent by weight of the tablet.

8. The pharmaceutically acceptable tablet of claim 6, wherein the amount of croscarmellose sodium employed in the intragranular excipient mixture ranges from about 1.5 to about 3.5 percent by weight of the tablet.

9. The pharmaceutically acceptable tablet of claim 6, wherein the amount of hypromellose employed in the intragranular excipient mixture ranges from about 2 to about 4 percent by weight of the tablet.

10. The pharmaceutically acceptable tablet of claim 1, wherein the amount of mannitol employed in the intragranular excipient mixture is from about 13.5 to about 14.5 percent by weight of the tablet, the amount of croscarmellose sodium employed in the intragranular excipient mixture is from about 2 to about 3 percent by weight of the tablet, and the amount of hypromellose employed in the intragranular excipient mixture is from about 2.5 to about 3.5 percent by weight of the tablet.

11. The pharmaceutically acceptable tablet of claim 1, wherein the extragranular excipient is selected from one or more of croscarmellose sodium and magnesium stearate.

12. The pharmaceutically acceptable tablet of claim 11, wherein the amount of croscarmellose sodium employed in the extragranular excipient mixture is from about 1.5 to about 3.5 percent by w t of the tablet.

13. The pharmaceutically acceptable tablet of claim 11, wherein the amount of magnesium stearate employed in the extragranular excipient mixture is from about 0.5 to about 1.5 percent by weight of the tablet.

14. The pharmaceutically acceptable tablet of claim 11, wherein the amount of croscarmellose sodium employed in the extragranular excipient mixture is from about 2 to about 3 percent by weight of the tablet and the amount of magnesium stearate is about 1 percent by weight of the tablet.

15. The pharmaceutically acceptable tablet of claim 1, wherein the amount of mannitol employed in the intragranular excipient mixture is from about 13.5 to about 14.5 percent by weight of the tablet, the amount of croscarmellose sodium employed in the intragranular excipient mixture is from about 2 to about 3 percent by weight of the tablet, and the amount of hypromellose employed in the intragranular excipient mixture is from about 2.5 to about 3.5 percent by weight of the tablet; and further wherein the amount of croscarmellose sodium employed in the extragranular excipient mixture ranges from about 2 to about 3 percent by weight of the tablet and the amount of magnesium stearate employed in the extragranular mixture is about 1 percent by weight of the tablet.

16. The pharmaceutically acceptable tablet according to claim 1, wherein said tablet further comprises a film coating.

17. The pharmaceutically acceptable tablet according to claim 1, wherein said tablet comprises about 500 mg of ezatiostat hydrochloride.

18. The pharmaceutically acceptable tablet according to claim 1, wherein said tablet comprises about 750 mg of ezatiostat hydrochloride.

19. The pharmaceutically acceptable tablet according to claim 1, wherein said tablet comprises about 1 g of ezatiostat hydrochloride.

20. The pharmaceutically acceptable tablet according to claim 1, wherein said tablet comprises about 1.25 g of ezatiostat hydrochloride.

21. The pharmaceutically acceptable tablet according to claim 1, wherein said tablet is stored in a container with a desiccant.

22. A pharmaceutically acceptable tablet comprising a crystalline ansolvate of ezatiostat hydrochloride, an intragranular excipient, and an extragranular excipient, wherein the crystalline ansolvate of ezatiostat hydrochloride comprises from about 75 to about 82 percent by weight of the tablet, wherein the intragranular excipient is selected from the group consisting of mannitol, croscarmellose sodium, and hypromellose, or a mixture thereof, and extragranular excipient is croscarmellose sodium and/or magnesium stearate and wherein the crystalline ansolvate of ezatiostat hydrochloride is form D.

* * * * *